(12) United States Patent
Rawson et al.

(10) Patent No.: US 7,507,742 B2
(45) Date of Patent: Mar. 24, 2009

(54) SPIROCYCLIC DERIVATIVES

(75) Inventors: David J. Rawson, Sandwich (GB); Nigel A. Swain, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/565,953

(22) Filed: Dec. 1, 2006

(65) Prior Publication Data
US 2007/0129388 A1    Jun. 7, 2007

Related U.S. Application Data

(60) Provisional application No. 60/791,186, filed on Apr. 10, 2006, provisional application No. 60/741,854, filed on Dec. 2, 2005.

(51) Int. Cl.
*A01N 43/54* (2006.01)
*A61K 31/517* (2006.01)
*C07D 237/00* (2006.01)
*C07D 239/00* (2006.01)
*C07D 241/00* (2006.01)

(52) U.S. Cl. .................. 514/266.3; 544/231
(58) Field of Classification Search ............ 544/231; 514/266.3
See application file for complete search history.

(56) References Cited

FOREIGN PATENT DOCUMENTS

| WO | WO 01/83772 A1 | 11/2001 |
|---|---|---|
| WO | WO 02/074754 A1 | 9/2002 |
| WO | 2004/026818 * | 1/2004 |
| WO | WO 2004/026818 A1 | 4/2004 |
| WO | WO 2006/092691 A1 * | 9/2006 |
| WO | WO 2006 092692 | 9/2006 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
West, Anthony R., Solid State Chemistry and Its Applicaitons, Wiley, New York, 1988, 358.*
Dermer, Bio/Technology, 1994, 12:320.*
Freshney, Culture of Animal Cells, A Manual of Basic Technique, Alan R. Liss, Inc., 1983.*
Bernardelli, et al., Spiroquinazolines as Novel, Potent, and Selective PDE7 Inhibitors. Part 2: Optimization of 5,8-disubstituted Derivatives, Bioorganic & Medicinal Chem. Letters, 14, 4627-31 (2004).*
Perez-Torres, et al., "Alterations on Phosphodiesterase Type 7 and 8 Isozyme mRNA Expression in Alzheimer's DIsease Brains Examined by in Situ Hydridization", Experimental Neurology, 2003, pp. 322-334, vol. 182.
Smith, et al., "Ubiquitous Expression of Phosphodiesterase 7A in Human Proinflammatory and Immune Cells", Am. J. Physiol. Lung Cell Mol. Physiol., 2003, pp. L279-L289, vol. 284.

Bloom, et al., "Identification and Tissue-specific Expression of PDE7 Phosphodiesterase Splice Variants", Proc. Natl. Acad. Sci. USA, 1996, p. 14188-14192, vol. 93, No. 24.
Gardner, et al., "Cloning and Characterization of the Human and Mouse PDE7B, a Novel cAMP-Specific Cyclic Nucleotide Phosphodiesterase", Biochemical and Biophysical Research Communications, 2000, pp. 186-192, vol. 272.
Glavas, et al., "T Cell Activation Up-regulates Cyclic Nucleotide Phosphodisterases 8A1 and 7A3", Proc. Natl. Acad. Sci. USA, 2007, pp. 6319-6324, vol. 98, No. 11.
Han, et al., "Alternative Splicing of the High Affinity cAMP-Specific Phosphodiesterase (PDE7A) mRNDA in Human Skeletal Muscle and Heart", J. Biol.Chem., 1997, pp. 16152-16157, vol. 272, No. 26.
Hetman, et al., "Cloning and Characterization of PDE7B, a cAMP-Specific Phosphodiesterase", Proc. Natl. Acad. Sci. USA, 2000, pp. 472-476, vol. 97, No. 1.
Ichimura, et al., "A New Cyclic Nucleotide Phosphodiesterase Isozyme Expressed in the T-lymphocyte Cell Lines", Biochem. Biophys. Res. Commun., 1993, pp. 985-990, vol. 193, No. 3.
Lee, et al., "PDE7A is expressed in Human B-lymphocytes and is Up-regulated by Elevation of Intracellular cAMP", Cellular Signalling, 2002, pp. 277-284, vol. 14.
Li, et al., "CD3- and CD28- Dependent Induction of PDE7 Required for T Cell Activiation", Science, 1999, pp. 848-851, vol. 283.

(Continued)

*Primary Examiner*—James O Wilson
*Assistant Examiner*—Erich A Leeser
(74) *Attorney, Agent, or Firm*—Gregg C. Benson; J. Michael Dixon

(57) ABSTRACT

The invention provides compounds of formula (I):

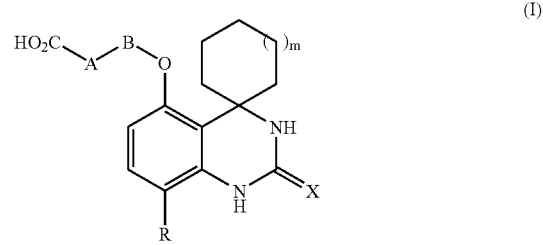

wherein:
m is 0, 1 or 2;
X is O, S or N—CN;
R is F, Cl or CN;
A is a $C_{3-6}$ cycloalkylene group optionally substituted with a $C_{1-4}$ alkyl group; and
B is a single bond or a $C_{1-2}$ alkylene group;
or a pharmaceutically acceptable salt, solvate, polymorph or prodrug thereof.

The compounds are PDE7 inhibitors and have a number of therapeutic applications, particularly in the treatment of pain, especially neuropathic pain.

13 Claims, 7 Drawing Sheets

OTHER PUBLICATIONS

Michaeli, et al., "Isolation and Characterization of a Previously Undetected Human cAMP Phosphodiesterase by Complementation of cAMP Phosphodiesterase-deficient Saccharomyces Cerevisiae", J. Biol. Chem., 1993, pp. 12925-12932, vol. 268, No. 17.

Miro, et al., "Differential Distribution of cAMP-Specific Phosphodiesterase 7A mRNA in Rat Brain and Peripheral Organs", Synapse, 2001, pp. 201-214, vol. 40.

International Preliminary Report on Patentability for PCT/IB2006/03388, dated Feb. 25, 2008.

Bernardelli, P. et al.; "Spiroquinazolinones as novel, potent, and selective PDE7 inhibitors. Part 2: . . .", Biorganic & Med. Chem. Lts., V. 14, No. 18, 2004, p.4627-4631.

* cited by examiner

SPIROCYCLIC DERIVATIVES

This application is a United States utility application, which claims the benefit of priority to U.S. Provisional Application No. 60/741,854, filed Dec. 2, 2005 and U.S. Provisional Application No. 60/791,186, filed Apr. 10, 2006.

FIELD OF THE INVENTION

This invention relates to spirocyclic derivatives, and to processes for the preparation of, intermediates used in the preparation of, compositions containing and the uses of, such derivatives.

The spirocyclic derivatives of the present invention are PDE7 inhibitors and have a number of therapeutic applications, particularly in the treatment of pain, especially neuropathic pain.

BACKGROUND TO THE INVENTION

Phosphodiesterases (PDEs) are a family of enzymes which affect various cellular signalling processes by the process of hydrolyzing the second messenger molecules cAMP and cGMP to the corresponding inactive 5'-monophosphate nucleotides and thereby regulating their physiological level. The secondary messengers cAMP and cGMP are responsible for the regulation of numerous intracellular processes. There are at least 11 families of PDE's, some (PDE3, 4, 7, 8) being specific for cAMP, and others for cGMP (PDE5, 6, and 9).

PDE7 is one member of the PDE family and comprises 2 subclass members PDE7 A and B. The mRNA of PDE7 is expressed in various tissues and cell types known to be important in the pathogenesis of several diseases such as T-cell related disorders. In particular PDE7A and its splice variants are upregulated in activated T-cells, (L. Li, C. Yee and J. A. Beavo, *Science* (1999), 283, 848-851), and in B-lymphocytes. (R. Lee, S. Wolda, E. Moon, J. Esselstyn, C. Hertel and A. Lerner, *Cell. Signal* (2002), 14, 277-284), autoimmune disease (L. Li et al, above), and airway disease (S. J. Smith et al, *Am. J. Physiol. Lung. Cell. Mol. Physiol.* (2003), 284, L279-L289). Consequently it is expected that selective inhibitors of PDE7 will have broad application as both immunosuppressants and treatment for respiratory conditions, for example chronic obstructive pulmonary disease and asthma (N. A. Glavas, C. Ostenson, J. B. Schaefer, V. Vasta and J. A. Beavo. *PNAS* (2001), 98, 6319-6324).

Studies in rat have shown that PDE7A mRNA is found to be widely distributed in rat brain in both neuronal and non-neuronal cell populations. The highest levels are observed in the olfactory bulb, olfactory tubercle, hippocampus, cerebellum, medial habenula nucleus, pineal gland, area postrema, and choroid plexus. PDE7A mRNA is also widely detected in other non brain tissue. These results are consistent with PDE7A being involved in the regulation of cAMP signaling in many brain functions and suggests that PDE7A could have an effect on memory, depression, and emesis (X. Miró, S. Pérez-Torres, J. M. Palacios, P. Puigdomènech, G. Mengod, *Synapse* (2001), 40, 201-214). A link to Alzheimer's disease is also suggested (S. Pérez Torres et al, *Experimental Neurology*, (2003) 182, 322-334). Additionally PDE7 has also been implicated in both fertility disorders (WO 01/83772) and leukaemia (R. Lee et al., *Cell Signalling* (2002) 14, 277-284).

PDE7A has been isolated from yeast (T. Michaeli et al, *J. Biol. Chem.* (1993) 268, 12925-12932), human (P. Han, Z. Xiaoyan and, M. Tamar, *J. Biol. Chem.* (1997) 272, 16152-16157), mouse (T. Bloom and J. A. Beavo, *Proc. Natl. Acad. Sci. USA* (1996), 93, 14188-14192) and upregulation of PDE7A levels is seen in human T lymphocytes (M. Ichimura and H. Kase. *Biochem. Biophys. Res. Commun.* (1993), 193, 985-990).

PDE7B, the second member of the PDE7 family, shares 70% amino acid homology with PDE7A in the C-terminal catalytic domain (N-terminal domain is the regulatory domain containing the phosphorylation site which is conserved across the PDE family). PDE7B is cAMP specific and has been cloned from mouse (accession number—AJ251858) and human (accession number—AJ251860) sources (C. Gardner, N. Robas, D. Cawkill and M. Fidock, *Biochem. Biophys. Res. Commun.* (2000), 272, 186-192). It has been shown to be expressed in a wide variety of tissues: the caudate nucleus, putamen and occipital lobe of the brain and peripherally in the heart, ovary and pituitary gland, kidney and liver small intestine and thymus, additionally in skeletal muscle, colon, bladder, uterus, prostate, stomach adrenal gland and thyroid gland. PDE7B has also been shown to discriminate among several general PDE inhibitors (J. M. Hetman, S. H. Soderling, N. A. Glavas and J. A. Beavo, *PNAS* (2000), 97, 472-476). However, many standard PDE inhibitors, such as zaprinast, rolipram and milrinone, do not specifically inhibit PDE7B.

Inhibitors of PDE7 are known as is their use in the treatment of various PDE7 related diseases. For example, WO 02/074754 describes compounds of formulae:

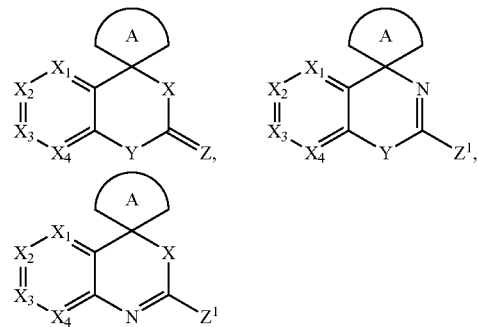

and their use in the treatment of PDE7-related disorders, such as T-cell-related diseases, autoimmune diseases, osteoarthritis, multiple sclerosis, osteoporosis, chronic obstructive pulmonary disease, asthma, cancer, acquired immune deficiency syndrome, allergy or inflammatory bowel disease.

WO 2004/026818 describes compounds of formula:

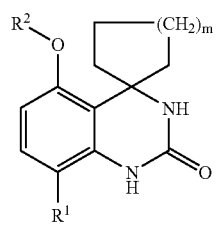

and their use in the treatment of PDE7-related disorders.

WO 2006/092691 describes the use of PDE7 inhibitors in the treatment of neuropathic pain.

We have surprisingly found that a class of compounds falling within the general disclosure of WO 02/074754, but not specifically disclosed or exemplified therein, exhibit unexpectedly superior pharmacokinetic properties when compared with the closest compound exemplified in WO 02/074754. These compounds are expected to exhibit reduced clearance from the body and have the potential to achieve a therapeutic effect when administered once a day.

SUMMARY OF THE INVENTION

The invention provides a compound of formula (I):

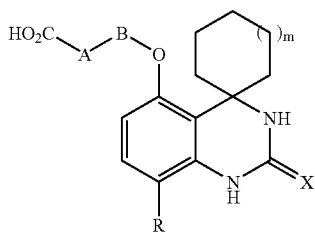

(I)

wherein:
m is 0, 1 or 2;
X is O, S or N—CN;
R is F, Cl or CN;
A is a $C_{3-6}$ cycloalkylene group optionally substituted with a $C_{1-4}$ alkyl group; and
B is a single bond or a $C_{1-2}$ alkylene group;

or a pharmaceutically acceptable salt, solvate, polymorph or prodrug thereof.

DETAILED DESCRIPTION OF PREFERRED EMBODIMENTS

Figure 1:
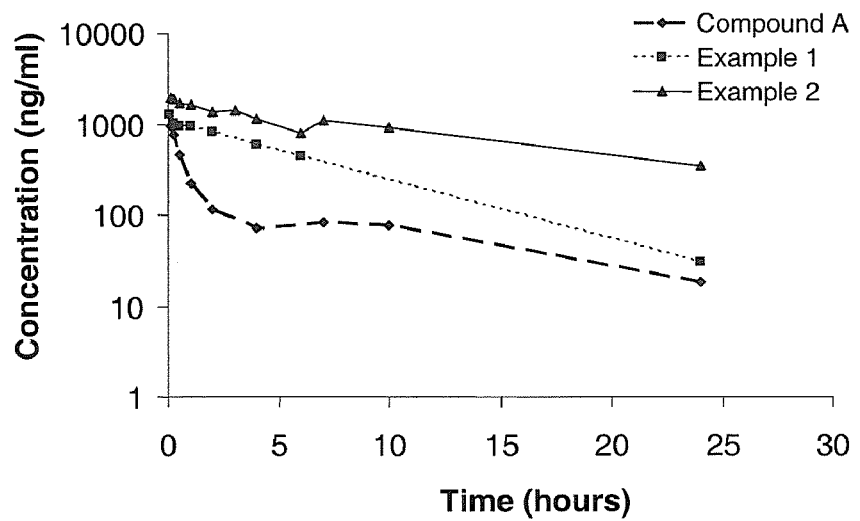
FIG. 1 is a concentration/time graph illustrating the mean, dose normalised, pharmacokinetic profiles of the compounds of Examples 1 and 2 of the present invention, as well as that of the compound of Example 75 of WO 02/074754 (Compound A), following 1 mg/kg intravenous administration.

In the context of the present invention, the term "alkylene" denotes a divalent saturated hydrocarbon chain having 1 or 2 carbon atoms. Examples of alkylene groups include methylene, ethylene and methylmethylene, of which methylene is preferred.

The term "cycloalkylene" denotes a divalent saturated carbocyclic ring having 3 to 6 carbon atoms. Examples of cycloalkylene groups include cyclopropylene (eg 1,1-cyclopropylene and cis- and trans-1,2-cyclopropylene), cyclobutylene (eg 1,1-cyclobutylene, cis- and trans-1,2-cyclobutylene, and cis- and trans-1,3-cyclobutylene), cyclopentylene (eg 1,1-cyclopentylene, cis- and trans-1,2-cyclopentylene, and cis- and trans-1,3-cyclopentylene) and cyclohexylene (eg 1,1-cyclohexylene, cis- and trans-1,2-cyclohexylene, cis- and trans-1,3-cyclohexylene) and cis- and trans-1,4-cyclohexylene). Preferred examples include cyclobutylene and cyclohexylene, more preferably cyclobutylene, even more preferably 1,3-cyclobutylene, and most preferably trans-1,3-cyclobutylene.

The term "alkyl" denotes a monovalent, straight or branched, saturated hydrocarbon chain containing 1 to 4 carbon atoms. Examples of alkyl groups include methyl, ethyl, n-propyl, isopropyl, n-butyl, isobutyl, sec-butyl and tert-butyl. Preferred examples include methyl and ethyl, especially methyl.

The cycloalkylene group is optionally substituted with a $C_{1-4}$ alkyl group. Preferably, the alkyl substituent, if present, is a methyl or ethyl group, more preferably a methyl group. The alkyl substituent, if present, may be present at any position on the ring, but is preferably present at the 1-position (ie the same position as the carboxylic acid group).

Preferably, m is 1 or 2, more preferably 1.
Preferably, X is O or N—CN, more preferably O.
Preferably, R is F or Cl, more preferably Cl.
Preferably, A is a cyclobutylene or cyclohexylene group optionally substituted with a methyl group. More preferably, A is a cyclobutylene group. Even more preferably, A is a 1,3-cyclobutylene group, especially a trans-1,3-cyclobutylene group.

Preferably, B is a single bond or a methylene group. More preferably, B is a single bond.

Particularly preferred compounds of the invention include those in which each variable in Formula (I) is selected from the suitable and/or preferred groups for each variable. Even more preferred compounds of the invention include those where each variable in Formula (I) is selected from the more preferred or most preferred groups for each variable.

The following compounds are especially preferred:

cis-3-[(8'-Chloro-2'-oxo-2',3'-dihydro-1'H-spiro[cyclohexane-1,4'-quinazolin]-5'-yl)oxy]cyclobutanecarboxylic acid;

trans-3-[(8'-Chloro-2'-oxo-2',3'-dihydro-1'H-spiro[cyclohexane-1,4'-quinazolin]-5'-yl)oxy]cyclobutanecarboxylic acid;

3-[(8'-fluoro-2'-oxo-2',3'-dihydro-1'H-spiro[cyclohexane-1,4'-quinazolin]-5'-yl)oxymethyl]cyclobutanecarboxylic acid;

trans-3-[(8'-cyano-2'-oxo-2',3'-dihydro-1'H-spiro[cyclohexane-1,4'-quinazolin]-5'-yl)oxy]cyclobutanecarboxylic acid;

1-[(8'-fluoro-2'-oxo-2',3'-dihydro-1'H-spiro[cyclohexane-1,4'-quinazolin]-5'-yl)oxymethyl]cyclobutanecarboxylic acid;

trans-3-[(8'-chloro-2'-oxo-2',3'-dihydro-1'H-spiro[cycloheptyl-1,4'-quinazolin]-5'-yl)oxy]cyclobutanecarboxylic acid;

trans-3-[(8'-chloro-2'-oxo-2',3'-dihydro-1'H-spiro[cyclopentyl-1,4'-quinazolin]-5'-yl)oxy]cyclobutanecarboxylic acid;

and pharmaceutically acceptable salts, solvates and prodrugs thereof.

The following compounds are especially preferred:

cis-3-[(8'-Chloro-2'-oxo-2',3'-dihydro-1'H-spiro[cyclohexane-1,4'-quinazolin]-5'-yl)oxy]cyclobutanecarboxylic acid;

trans-3-[(8'-Chloro-2'-oxo-2',3'-dihydro-1'H-spiro[cyclohexane-1,4'-quinazolin]-5'-yl)oxy]cyclobutanecarboxylic acid;

and pharmaceutically acceptable salts, solvates, polymorphs and prodrugs thereof.

The compound trans-3-[(8'-chloro-2'-oxo-2',3'-dihydro-1'H-spiro[cyclohexane-1,4'-quinazolin]-5'-yl)oxy]cyclobutanecarboxylic acid, and pharmaceutically acceptable salts, solvates, polymorphs and prodrugs thereof, particularly as the unsolvated crystalline form (Form A), described hereinbelow, and as the acetic acid solvate, described hereinbelow, are most preferred.

In one embodiment, the invention comprises the compound trans-3-[(8'-chloro-2'-oxo-2',3'-dihydro-1'H-spiro[cyclohexane-1,4'-quinazolin]-5'-yl)oxy]-cyclobutanecarboxylic acid, in an unsolvated crystalline form (Form A) characterised by the following powder X-ray diffraction peaks (2θ, in degrees±0.1°) when measured using Cu Kα radiation (Wavelength=1.5406 Å): 6.3, 17.8, 21.5, 22.1, 22.4, 26.3.

In another embodiment, the invention comprises the compound trans-3-[(8'-chloro-2'-oxo-2',3'-dihydro-1'H-spiro[cyclohexane-1,4'-quinazolin]-5'-yl)oxy]-cyclobutanecarboxylic acid, as an acetic acid solvate, characterised by the following powder X-ray diffraction peaks (2θ, in degrees ±0.1°) when measured using Cu Kα radiation (Wavelength=1.5406 Å): 8.3, 10.8, 16.6, 17.1, 19.5, 20.5, 23.7.

The invention further comprises a pharmaceutical composition comprising a compound of formula (I), either in its broadest aspect or a preferred aspect, or a pharmaceutically acceptable salt, solvate, polymorph or prodrug thereof, and a pharmaceutically acceptable carrier or diluent.

The invention further comprises a compound of formula (I), either in its broadest aspect or a preferred aspect, or a pharmaceutically acceptable salt, solvate, polymorph or prodrug thereof, for use as a medicament.

The invention further comprises use of a compound of formula (I), either in its broadest aspect or a preferred aspect, or a pharmaceutically acceptable salt, solvate, polymorph or prodrug thereof, in the manufacture of a medicament for the treatment of diseases or conditions for which therapy by a PDE7 inhibitor is relevant.

The invention further comprises a method of treating a disease or condition for which therapy by a PDE7 inhibitor is relevant, comprising administering an effective amount of a compound of formula (I), either in its broadest aspect or a preferred aspect, or a pharmaceutically acceptable salt, solvate, polymorph or prodrug thereof.

The compounds of formula (I), being PDE7 inhibitors, are potentially useful in the treatment of a range of disorders. The treatment of pain, particularly neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, *Prog. Neurobiol.*, (1999), 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (eg painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, *Science*, (2000), 288,1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, *Lancet*, (1999) 353, 1959-1964). The symptoms of neuropathic pain are difficult to treat, as they are often heterogeneous even between patients with the same disease (Woolf & Decosterd, *Pain Supp.*, (1999), 6, S141-S147; Woolf and Mannion, above). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, *Ann Pharmacother.*, (2002), 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

The compounds of formula (I) of the present invention are also useful in the treatment of conditions other than pain. In particular, the compounds of formula (I) of the present invention are useful in the treatment of T-cell-related diseases, autoimmune diseases, multiple sclerosis, osteoporosis, chronic obstructive pulmonary disease, asthma, cancer, acquired immune deficiency syndrome (AIDS), allergy and inflammatory bowel disease.

The invention further comprises use of a compound of formula (I), either in its broadest aspect or a preferred aspect, or a pharmaceutically acceptable salt, solvate or prodrug thereof, in the manufacture of a medicament for the treatment of a condition or disorder selected from pain (especially neuropathic pain), T-cell-related diseases, autoimmune diseases, multiple sclerosis, osteoporosis, chronic obstructive pulmonary disease, asthma, cancer, acquired immune deficiency syndrome (AIDS), allergy and inflammatory bowel disease.

The invention further comprises a method of treating a disease or condition selected from pain (especially neuropathic pain), T-cell-related diseases, autoimmune diseases, multiple sclerosis, osteoporosis, chronic obstructive pulmonary disease, asthma, cancer, acquired immune deficiency syndrome (AIDS), allergy or inflammatory bowel disease, comprising administering an effective amount of a compound of formula (I), either in its broadest aspect or a preferred aspect, or a pharmaceutically acceptable salt, solvate or prodrug thereof.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. The present invention embraces both the unsolvated and all solvated forms.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Hereinafter all references to compounds of formula (I) include references to salts and solvates thereof and to solvates of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labelled compounds of formula (I).

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in *Pro-druqs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

The compounds of formula (I) of the present invention contain a carboxylic acid functionality (—COOH). Therefore, suitable prodrugs comprise esters thereof, wherein the hydrogen of the carboxylic acid functionality of the compound of formula (I) is replaced by an ester residue. The term "ester residue" means an ester group which can be cleaved in vivo by a biological method such as hydrolysis and forms a compound of formula (I) having the free carboxylic acid group or a salt thereof.

Whether a compound is such a prodrug or not can, for example, be determined by administering it by intravenous injection to an experimental animal, such as a rat or mouse, and then studying the body fluids of the animal to determine whether or not the compound of formula (I) or a pharmaceutically acceptable salt thereof can be detected.

Preferred examples of the ester residue include:

$C_{1-20}$ alkyl groups, which may be straight or branched chain alkyl groups such as methyl, ethyl, n-propyl, isopropyl, n-butyl, isobutyl, sec-butyl, tert-butyl, n-pentyl, isopentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl and icosanyl, especially $C_{1-12}$ alkyl groups, preferably $C_{1-8}$ alkyl groups, more preferably $C_{1-6}$ alkyl groups, and most preferably $C_{1-4}$ alkyl groups such as those defined and exemplified above;

$C_{1-10}$ haloalkyl groups (defined as an alkyl group substituted by one or more halogen atoms, preferably fluorine or chlorine atoms, more preferably fluorine atoms), preferably $C_{1-8}$ haloalkyl groups, more preferably $C_{1-6}$ haloalkyl groups, and most preferably $C_{1-4}$ haloalkyl groups such as mono-, di- or trifluoromethyl, mono-, di- or trichloromethyl, bromomethyl, 2-fluoroethyl, 2,2-difluoroethyl, 2,2,2-trifluoroethyl, 2-chloroethyl, 2,2-dichloroethyl, 2,2,2-trichloroethyl, perfluoroethyl, perfluoropropyl and perfluorobutyl;

$C_{1-10}$ hydroxyalkyl groups (defined as an alkyl group substituted by a hydroxy (—OH) group), preferably $C_{1-8}$ hydroxyalkyl groups, more preferably $C_{1-6}$ hydroxyalkyl groups, and most preferably $C_{1-4}$ hydroxyalkyl groups such as hydroxymethyl, 1- or 2-hydroxyethyl, 1-, 2- or 3-hydroxypropyl, and 1-, 2-, 3- or 4-hydroxybutyl;

($C_{1-10}$ alkoxy)$C_{1-10}$ alkyl groups (defined as an alkyl group substituted by an alkoxy group), preferably ($C_{1-6}$ alkoxy)$C_{1-6}$ alkyl groups, more preferably ($C_{1-4}$ alkoxy)$C_{1-4}$ alkyl groups, and most preferably ($C_{1-4}$ alkoxy)methyl groups, such as the methoxymethyl, 1,1-dimethyl-1-methoxymethyl, ethoxymethyl, propoxymethyl, isopropoxymethyl, butoxymethyl and t-butoxymethyl groups;

$C_{1-6}$ alkoxylated ($C_{1-6}$ alkoxy)methyl groups, such as the 2-methoxyethoxymethyl group;

halo($C_{1-6}$ alkoxy)methyl groups, such as the 2,2,2-trichloroethoxymethyl and bis(2-chloroethoxy)methyl groups;

$C_{3-8}$ cycloalkyl groups, such as cyclopropyl, cyclobutyl, cyclopentyl, cyclohexyl, cycloheptyl and cyclooctyl groups;

aralkyl groups, for example: $C_{1-6}$ alkyl groups substituted by from 1 to 3 $C_{6-14}$ aryl groups (wherein the aryl part is selected from phenyl, naphthyl, anthryl and phenanthryl), such as the benzyl, α-naphthylmethyl, β-naphthylmethyl, diphenylmethyl, triphenylmethyl, α-naphthyldiphenylmethyl and 9-anthrylmethyl groups; and $C_{1-6}$ alkyl groups substituted by from 1 to 3 substituted $C_{6-14}$ aryl groups, where one or more of the aryl groups is substituted by one or more (preferably 1 to 3, and more preferably only 1) $C_{1-6}$ alkyl, $C_{1-6}$ alkoxy, nitro, halogen or cyano substituents, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; especially the benzyl group;

tetrahydropyranyl or tetrahydrothiopyranyl groups, wherein the tetrahydropyranyl or tetrahydrothiopyranyl group may be optionally substituted with a substituent selected from halo and $C_{1-6}$ alkoxy, such as: tetrahydropyran-2-yl, 3-bromotetrahydropyran-2-yl, 4-methoxy-tetrahydropyran-4-yl, tetrahydrothiopyran-2-yl, and 4-methoxy-tetrahydrothiopyran-4-yl groups;

tetrahydrofuranyl or tetrahydrothiofuranyl groups, wherein the tetrahydrofuranyl or tetrahydrothiofuranyl group may be optionally substituted with a substituent selected from halo and $C_{1-6}$ alkoxy, such as: tetrahydrofuran-2-yl and tetrahydrothiofuran-2-yl groups;

$C_{2-10}$ alkenyl groups, such as the vinyl, propenyl, butenyl, pentenyl, hexenyl, heptenyl, octenyl, nonenyl and decenyl groups; and $C_{2-10}$ alkynyl groups, such as ethynyl, propynyl, butynyl, pentynyl, hexynyl, heptynyl, octynyl, nonynyl and decynyl groups.

Further examples of replacement groups in accordance with the foregoing examples and examples of other prodrug types may be found in the aforementioned references.

Moreover, certain compounds of formula (I) may themselves act as prodrugs of other compounds of formula (I).

Compounds of formula (I) containing one or more asymmetric carbon atoms can exist as two or more stereoisomers. As the compounds of formula (I) contain a cycloalkylene group, cis/trans isomers are possible when the $CO_2H$ and B groups are not on the same carbon. Where structural isomers are interconvertible via a low energy barrier, tautomeric isomerism ('tautomerism') can occur. This can take the form of proton tautomerism in compounds of formula (I) containing a cyclic urea, thiourea or cyanoguanidine group, or so-called valence tautomerism in compounds which contain an aromatic moiety. It follows that a single compound may exhibit more than one type of isomerism.

Included within the scope of the present invention are all stereoisomers, diastereoisomers (especially cis/trans isomers) and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as 35S.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of formula (I) as hereinbefore defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of compound of formula (I) which provides the best combination of features for this purpose. Such features include the melting point, solubility, process- ability and yield of the intermediate form and the resulting ease with which the product may be purified on isolation.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulphate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated - see, for example, *J. Pharm. Sci.*, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, ie. as a carrier, diluent, or solubiliser. Most commonly used for these purposes are alpha-, beta- and gamma-cyclodextrins, examples of which may be found in WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 10 mg to 1000 mg depending, of course, on the mode of administration. For example, oral administration may require a total daily dose of from 10 mg to 1000 mg, while an intravenous dose may require from 10 mg to 1000 mg. The total daily dose may be administered in single or divided doses and may, at the doctor's discretion, fall outside of the typical range given herein.

These dosages are based on an average human subject having a weight of about 60 kg to 70 kg. The doctor will readily be able to determine doses for subjects whose weight falls outside this range, such as infants and the elderly.

For the avoidance of doubt, references herein to "treatment" include references to curative, palliative and prophylactic treatment.

All of the compounds of formula (I) can be prepared by the procedures described in the General Methods described below or by the specific methods described in the Examples section and the Preparations section, or by routine modifications thereof. The present invention also encompasses any one or more of these processes for preparing the compounds of formula (I), in addition to any novel intermediates used therein.

General Methods

The following abbreviations are used:
DMF=dimethylformamide
DMSO=dimethyl sulphoxide
TEMPO=2,2,6,6-tetramethylpiperidine-N-oxide
THF=tetrahydrofuran
DCM=dichloromethane The compounds of formula (I) may be prepared as shown in Scheme 1 below.

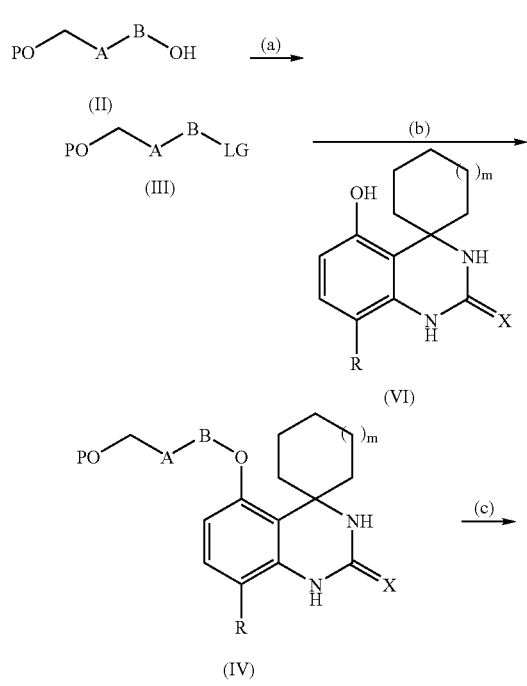

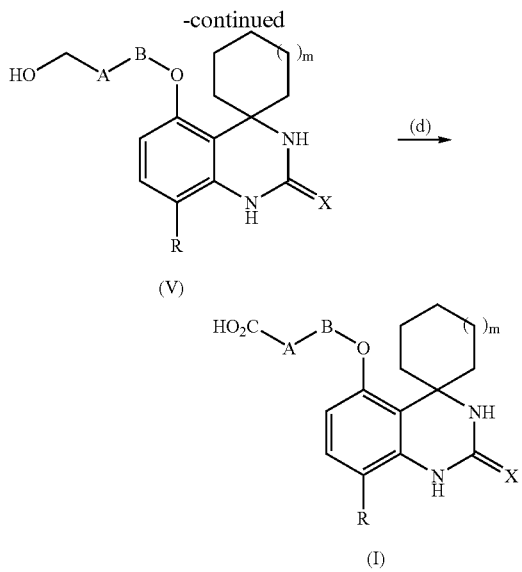

In Scheme 1, P represents a hydroxy-protecting group, suitable examples of which are described in "Protective Groups in Organic Synthesis" by T. W. Greene and P. Wuts, Wiley and Sons, 1991, and LG represents a suitable leaving group, such as halogen, ($C_{1-6}$ alkyl)sulphonyloxy (eg methane-sulphonyloxy), ($C_{1-6}$ haloalkyl)sulphonyloxy (eg trifluoromethanesulphonyloxy) or benzene- or toluenesulphonyloxy (eg p-toluenesulphonyloxy). Preferably P is benzyl and LG is p-toluenesulphonyloxy.

Step (a): The compound of formula (III) may be prepared from compound (II) and an appropriate agent capable of converting a hydroxy group into a leaving group, typically a sulphonylating reagent (eg methanesulphonyl chloride or p-toluenesulphonyl chloride) in the presence of a base (eg triethylamine or pyridine) in a suitable solvent (eg pyridine or dichloromethane) at 0° C. to room temperature for 15 minutes to 24 hours.

Preferred conditions are: 1 eq compound (II) in dichloromethane, 1.2 eq p-toluenesulphonyl chloride, 2 eq pyridine at room temperature for 18 hours.

Step (b): The compound of formula (IV) may be prepared from compound (III) and the hydroxy compound of formula (VI) in a suitable solvent (eg DMF, DMSO) in the presence of a suitable base (eg $Cs_2CO_3$, $K_2CO_3$), optionally in the presence of a crown ether (eg 18-crown-6) at 50-120° C. overnight.

Preferred conditions are: 1 eq compound (VI), 1.1 eq compound (III), 1.2 eq $Cs_2CO_3$, in DMF at 80° C. for 24 hours.

Compounds of formula (VI) are generally described in WO 02/074754. Specific compounds of formula (VI) wherein X is O, m is 1 and R is Cl may be prepared as described in *Bioorg. Med. Chem. Lett.*, (2004), 14 (18), 4627-32, or as outlined in Scheme 5 below.

Step (c): The compound of formula (IV) may be deprotected by reaction with a deprotecting agent in a suitable solvent to yield the compound of formula (V). Suitable reagents and methods are described in "Protective Groups in Organic Synthesis" (referred to above). When P is benzyl, examples of suitable reagents include boron trichloride or iron (III) chloride.

Preferred conditions are: 1 eq compound (IV) in dichloromethane, 4 eq $BCl_3$ at room temperature for 18 hours.

Step (d): The compound of formula (I) may be prepared by oxidation of the compound of formula (V) using an oxidising agent in a suitable solvent. Typical reagents and conditions include catalytic chromium trioxide and periodic acid ($H_5IO_6$) in a solvent such as acetonitrile at room temperature to 50° C. for 18 to 36 hours, or alternatively NaOCl plus $NaClO_2$ in the presence of catalytic TEMPO in a solvent such as acetonitrile at 0° C. to room temperature for 18 to 36 hours.

Preferred conditions are: 1 eq compound (V), 2.5 eq periodic acid, 0.02 eq $CrO_3$, in 0.75% aqueous acetonitrile, 24 hours at 40° C.

The compounds of formula (I) may alternatively be prepared by oxidation of compounds of formula (V) in a two-step procedure via the aldehydes of formula (VII) as shown in Scheme 2.

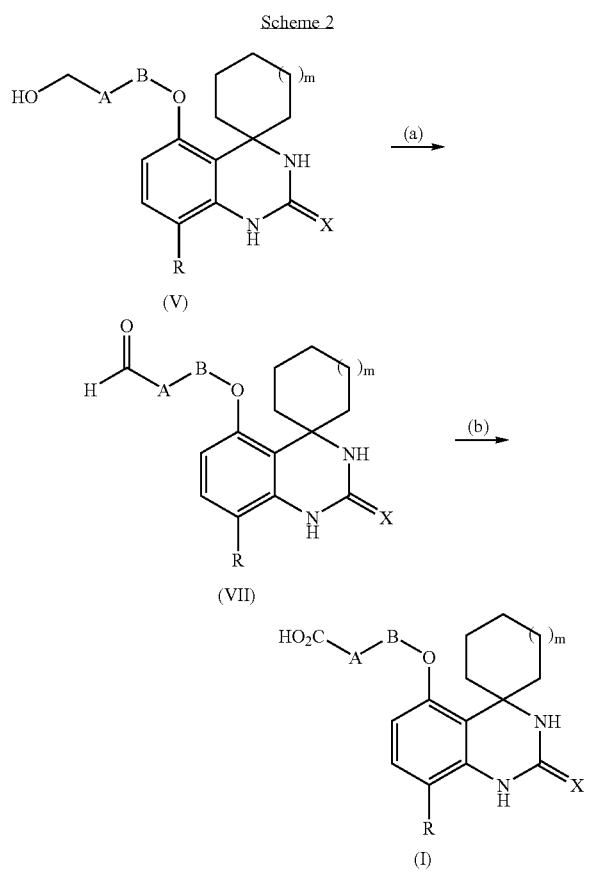

Step (a): Oxidation of the alcohol (V) to the aldehyde (VII) is typically carried out using NaOCl with catalytic TEMPO in a suitable solvent, eg acetonitrile, acetone at 0° C. to room temperature for 2-18 hours, or alternatively using sulphur trioxide-pyridine complex with DMSO in a solvent such as THF at 0° C. to room temperature for 2-18 hours.

Step (b): Further oxidation of the aldehyde (VII) to the acid (I) with is typically carried out using $NaClO_2$ in the presence of potassium phosphate in a solvent such as aqueous t-butanol at 0° C. to room temperature for 2-18 hours, or alternatively using trichloroisocyanuric acid with catalytic TEMPO in a suitable solvent, eg acetone or acetonitrile, at 0° C. to room temperature for 2-18 hours.

Compounds of formula (II) are known in the literature. For example, compounds of formula (II) wherein A is a cis-1,3- cyclobutylene group and B is a single bond may be prepared as described in *J. Chem. Soc., Perkin Trans.* 1, (1995), 18, 2281-7.

Alternatively compounds of formula (Ib), which are compounds of formula (I) wherein A is a cis- or trans-1,3-cyclobutylene group and B is a single bond may be prepared from compound (VII) or compound (IX) by standard methods, such as shown in Scheme 3. Trans compounds (II) and (X) may be obtained from cis compounds (II) and (X) respectively by inversion using Mitsunobu chemistry analogous to that described in *Synthesis*, (1981), 1.

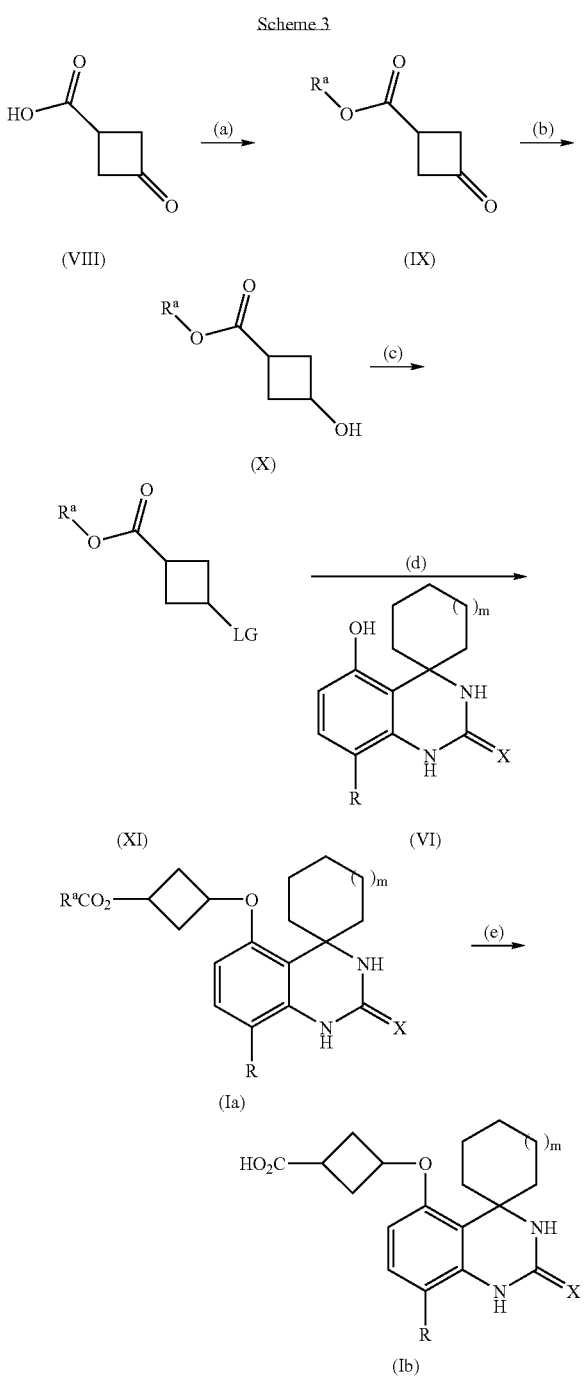

In Scheme 3, $R^a$ is an ester residue, suitable examples of which are described above with reference to prodrugs and in "Protective Groups in Organic Synthesis" (referred to above) (eg ($C_{1-6}$)alkyl, benzyl or (+) or (−)-menthyl), and LG is a leaving group such as halogen, ($C_{1-6}$ alkyl)sulphonyloxy (eg methanesulphonyloxy), ($C_{1-6}$ haloalkyl)sulphonyloxy (eg trifluoromethanesulphonyloxy) or benzene- or toluenesulphonyloxy (eg p-toluenesulphonyloxy).

Step (a): The compound of formula (IX) may be prepared by reaction of compound (VII) with a suitable alcohol of formula $R^a$OH (eg methanol, t-butanol, benzyl alcohol or (−) menthol) under a variety of conditions, suitable examples of which are described in "Protective Groups in Organic Synthesis" (referred to above).

Preferred conditions are: 1 eq compound (VIII), 1.1 eq. 1,1'-carbonyl diimidazole, in ethyl acetate at reflux for 1 hour followed by 1 eq $R^a$OH at room temperature for 4 hours.

Step (b): Reduction of compound (IX) to the alcohol (X) may be carried out using a suitable reducing agent, eg sodium borohydride or L-Selectride®, in a suitable solvent such as THF.

Preferred conditions are: 1 eq compound (IX), 0.5 eq $NaBH_4$ in 20:1 THF:methanol at 0° C. for 20 minutes.

Step (c): The compound of formula (XI) may be prepared from compound (X) using reagents and conditions similar to those described in Scheme 1, step (a).

Preferred conditions are: 1 eq compound (X), 1.05 eq p-toluenesulphonyl chloride in pyridine at 0° C. to room temperature.

Step (d): The compound of formula (Ia) may be prepared from compound (XI) and the hydroxy compound of formula (VI) using reagents and conditions similar to those described in Scheme 1, step (b).

Preferred conditions are: 1.2 eq compound (XI), 1.0 eq compound (VI), 1.5 eq $Cs_2CO_3$ in DMF at 80° C. for 18 hours.

Step (e): The compound of formula (Ia) may be hydrolysed to provide the compound of formula (Ib). This reaction may be achieved under a variety of conditions, suitable examples of which are described in "Protective Groups in Organic Synthesis" (referred to above). Preferred conditions are: compound (Ia), 2 eq NaOH in 1:1 ethanol:water at 60° C. for 2 hours.

Compound (VIII) is described in *J. Org. Chem.*, (1981), 53, 3841-43 and compound (IX), wherein $R^a$ is a methyl group, is described in *J. Org. Chem.*, (1994), 59, 2132-34.

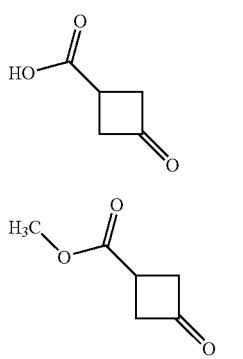

Compounds of formula (Id), which are compounds of formula (I) wherein B is a methylene group, may be prepared as shown in Scheme 4.

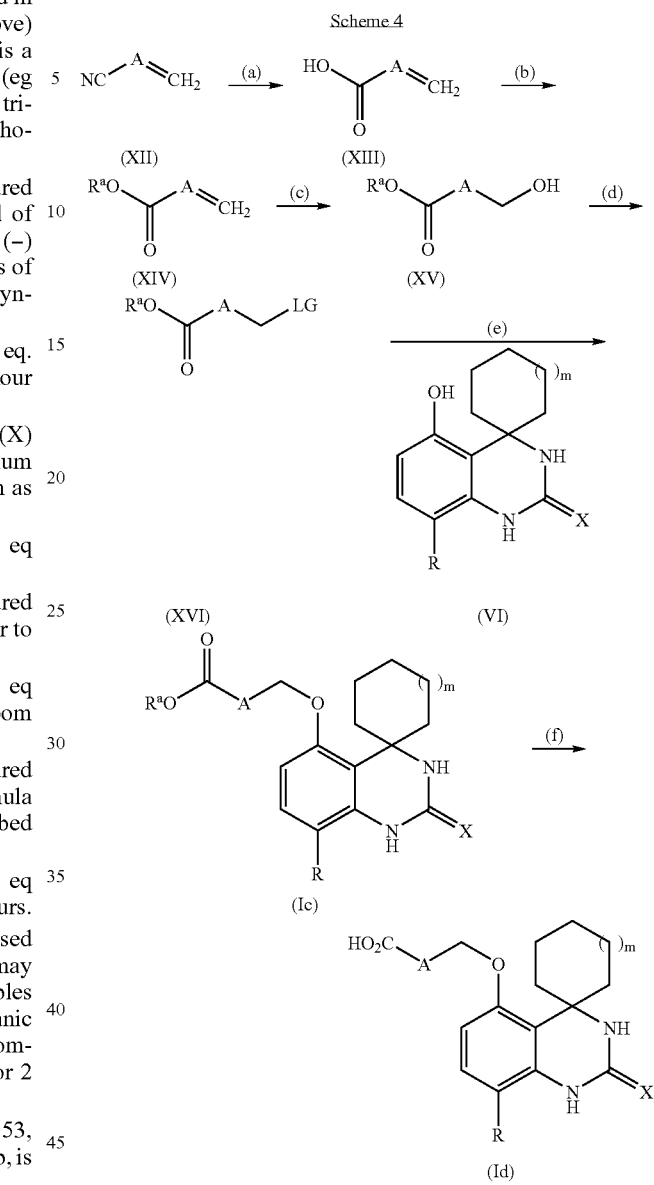

In Scheme 4, $R^a$ is an ester residue, suitable examples of which are described above with reference to prodrugs and in "Protective Groups in Organic Synthesis" (referred to above) (eg ($C_{1-6}$) alkyl or benzyl), and LG is a leaving group such as halogen or ($C_{1-6}$ alkyl)sulphonyloxy (eg methanesulphonyloxy), ($C_{1-6}$ haloalkyl)sulphonyloxy (eg trifluoromethanesulphonyloxy) or benzene- or toluenesulphonyloxy (eg p-toluenesulphonyloxy). Preferably $R^a$ is benzyl and LG is p-toluenesulphonyloxy. Compounds of formula (XII) may be obtained commercially.

Step (a): The compound of formula (XIII) may be prepared by hydrolysis of the compound of formula (XII) under acidic or basic conditions, eg aqueous sodium hydroxide with a suitable co-solvent such as methanol, ethanol or 1,4-dioxane, or aqueous hydrochloric acid or sulphuric acid with optionally a suitable co-solvent such as ethanol or 1,4-dioxane.

Preferred conditions are: 1 eq compound (XII), 4 eq NaOH, in 1:1 ethanol:water at reflux for 2.5 hrs.

Step (b): The compound of formula (XIV) may be prepared by reaction of the compound of formula (XIII) with a suitable alcohol of formula R$^a$OH (eg methanol, tert-butanol, benzyl alcohol) under a variety of conditions, suitable examples of which are described in "Protective Groups in Organic Synthesis" (referred to above). Preferred conditions are: 1 eq compound (XIII), 1.1 eq 1,1'-carbonyldiimidazole in ethyl acetate for about 1 hour followed by 1.2 eq benzyl alcohol at room temperature for 18 hours.

Step (c): The compound of formula (XV) may be prepared by treatment of the compound of formula (XIV) with a hydroborating agent such as borane-dimethylsulphide, catecholborane or 9-borabicyclo[3.3.1]nonane (9-BBN) in a suitable solvent such as THF at 0° C.-room temperature followed by in situ oxidation with an oxidant such as hydrogen peroxide, sodium perborate or trimethylamine-N-oxide at room temperature to 60° C.

Preferred conditions are: 1 eq compound (XIV), 0.5 eq borane-dimethylsulphide, in THF at room temperature for 1 hour followed by 1.2 eq sodium perborate and heating at 60° C. for 1 hour.

Step (d): The compound of formula (XVI) may be prepared from the compound of formula (XV) using reagents and conditions similar to those described in Scheme 1, step (a).

Preferred conditions are: 1 eq compound (XV), 1.3 eq p-toluenesulphonyl chloride, 2.6 eq pyridine in DCM at 0° C. to room temperature.

Step (e): The compound of formula (Ic) may be prepared from the compound of formula (XVI) and the hydroxy compound of formula (VI) using reagents and conditions similar to those described in Scheme 1, step (b).

Preferred conditions are: 1.2 eq compound (XVI), 1.0 eq compound (VI), 1.5 eq Cs$_2$CO$_3$ in DMF at 80° C. for 18 hours.

Step (f): The compound of formula (Ic) may be hydrolysed to provide the compound of formula (Id). This reaction may be achieved under a variety of conditions, suitable examples of which are described in "Protective Groups in Organic Synthesis" (referred to above).

Preferred conditions are: compound (Ic), excess NaOH in 1:1 ethanol:water at 60° C. for 2 hours.

Compounds of formula (VI) are generally described in WO 02/074754. Specific compounds of formula (VIa), which are compounds of formula (VI) wherein X is O or S, may be prepared as described in *Bioorg. Med. Chem. Lett.*, (2004), 14 (18), 4627-32, or as outlined in Scheme 5 below.

Scheme 5

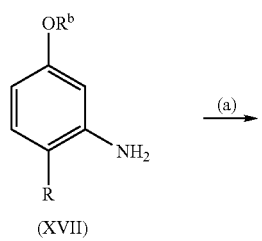

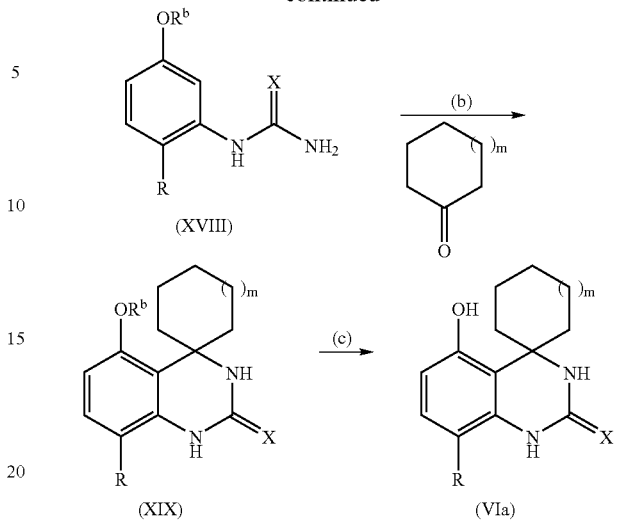

In Scheme 5, R$^b$ is (C$_{1-6}$)alkyl or benzyl.

Step (a): Compounds of formula (XVIII) may be prepared by the reaction of an aniline (XVII) with sodium or potassium cyanate or thiocyanate in a suitable solvent or solvent mixture for example dichloromethane or acetic acid:water in the presence of an acid such as maleic or acetic acid. Alternatively the compounds of formula (XVIII) may be prepared by reaction of an aniline (XVII) with trimethylsilyl isocyanate or thiocyanate in a solvent such as dichloromethane followed by in situ hydrolysis with water.

Preferred conditions when X is O are: 1 eq compound (XVII) in acetic acid:water (9:1) followed by 1.2 eq potassium cyanate in water dropwise and held at 40° C. for 1 hour.

Step (b): Compounds of formula (XIX) may be prepared by the reaction of a urea of formula (XVIII) and the appropriate ketone in the presence of a dehydrating agent such as polyphosphoric acid or Eaton's reagent (7.5% P$_2$O$_5$ in methanesulphonic acid) at between 50 and 100° C.

Preferred conditions are: 1 eq compound (XVIII), Eaton's reagent (30 g/g) at 60° C., followed by 2 eq ketone and heating at 80° C. for 1 hour.

Step (c): The compound of formula (VIa) may be prepared by reaction of a compound of formula (XIX) with a Lewis acid such as boron tribromide in a suitable solvent such as dichloromethane at room temperature or by reaction with a strong acid at high temperature, for example hydrobromic acid at 110° C.

Preferred conditions are: 1 eq compound (XIX), 20 eq 48% aqueous hydrogen bromide, in acetic acid at 110° C. for 4 days.

The PDE7 inhibitors of formula (I) may be usefully combined with another pharmacologically active compound, or with two or more other pharmacologically active compounds, particularly in the treatment of pain. For example, a PDE7 inhibitor of formula (I), or a pharmaceutically acceptable salt, solvate or prodrug thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion®) or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5-HT_{1B/1D}$ agonist such as eletriptan, sumatriptan, naratriptan, zolmitriptan or rizatriptan;

a $5-HT_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro -2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl -2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6)S-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl] thio]-5-thiazolebutanol, 2-[[(1R,3S)-3-amino-4-hydroxy-1-(5-thiazolyl) butyl]thio]-6-(trifluoromethyl)-3pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl) -cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

The ability of the compounds of formula (I) to inhibit PDE7 may be measured using the following assay protocol.

PDE7A and PDE7B enzymes catalyse the hydrolysis of 3',5'-cyclic adenosine monophosphate (cAMP) to the 5'adenosine monophosphate, 5'AMP. In a multiwell plate; PDE enzyme, [$^3$H]-cAMP and the tested compounds, are incubated at room temperature. The incubation is terminated by addition of commercially available yttrium silicate scintillation proximity assay (SPA) beads containing zinc sulphate. The yttrium silicate beads preferentially bind linear nucleotides, thus the product of the enzyme reaction, [$^3$H]-5'AMP binds to the bead to produce a light signal, which is detected by a scintillation counter. The amount of signal produced directly correlates with the amount of product formed, and thus the activity of the enzyme. The maximum signal is obtained where enzyme and substrate are incubated alone. The background signal is measured from wells either containing no enzyme, or from wells containing a supramaximal concentration of a known PDE7A/B inhibitor. Each purified batch of enzyme is quality controlled and its $K_m$, $V_{max}$ and specific activity determined from kinetic studies before use in compound inhibition studies. The inhibition of the enzyme, by a test compound, is calculated relative to the maximum and background responses. Using these data a % inhibition value is calculated relative to the maximum and minimum values obtained.

Preparation of Working Solutions

A 1000 ml stock of buffer was prepared from the ingredients shown in Table 1 below:

TABLE 1

| Reagent | Source | Final concentration | Stock Soln. concentration | ml/ 1000 ml |
| --- | --- | --- | --- | --- |
| HEPES (buffer) | Sigma | 50 mM | 1 | 50 |
| MgCl$_2$ | Sigma | 5 mM | 1 | 5 |
| Pluronic ® (detergent) | Sigma | 0.025% | 5% | 5 |
| Millipore ® 18 mΩ purified water | Millipore | | | 940 |

The stock buffer was adjusted to pH 7.4 at room temperature and then filtered through a 0.2 μm filter. The stock buffer is stable at 4° C. for 1 month from the date of preparation.

On the day of experiment, Bovine Serum Albumin (BSA, available from Sigma) was added to the required volume of buffer to create a 0.00625% BSA final solution. This was achieved by preparing a stock 10% BSA solution as follows:

Preparation of Stock 10% BSA Solution 1 g BSA was dissolved in 10 ml purified water, mixed by inversion to ensure homogeneity and aliquot in 100 μl volumes in appropriately labelled tubes. The 10% BSA solution is stable at −20° C. for up to 6 months.

An aliquot of the stock 10% BSA stock solution was removed from storage and allowed to thaw out at room temperature before being used to create the BSA working solution as shown in Table 2 below:

Preparation of 10 ml Working BSA Assay Buffer

TABLE 2

| Reagent | Volume | Final BSA concentration |
| --- | --- | --- |
| 1x Buffer stock | 9.99 ml | |
| 10% BSA stock | 6.25 μl | 0.00625% |

Preparation of Standard Compound and Controls

The compound of Example 75 of WO 02/074754, 5'-carboxypropoxy-8'-chloro-spiro[cyclohexane-1-4'-(3',4'-dihydro)quinazolin]-2'(1'H)-one (hereinafter "Compound A") was used as a standard.

4 mM stock solution prepared in 100% DMSO can be stored at 4° C. The volume of DMSO can be calculated as follows:

$$\text{Volume of } DMSO(\text{ml}) = \frac{\text{weight of compound}}{\text{Molecular weight of compound}} \times 250$$

The 30× Max control is a solution of 100% DMSO. The 30× Min control is achieved using a 30 µM of Compound A in 100% DMSO to yield no enzyme activity. 5 ml of a 30 µM solution of Compound A can be prepared by adding 4.962 ml of 100% DMSO to 37.5 µl of 4mM Compound A.

Method

On the day of assay, the 1× final assay buffer was prepared as detailed previously and kept on ice until needed.

Kinetic Studies

For each new batch of enzyme, the $K_m$ was determined, and the amount of enzyme required to obtain ~1000 cpm signal in 45 minutes, whilst remaining in the linear portion of the reaction progress curve, was assessed. Ideally <10% of available [$^3$H]-cAMP will be hydrolysed during the course of the assay.

Enzyme Solution

The optimisation of this assay has been carried out using cell lysate containing full length PDE7A and PDE7B enzyme. The concentration of the enzyme in this cell lysate sample is unknown, so the specific activity of the cell lysate is used as a measure to ensure that the same activity per well is used despite any batch-to-batch variation of concentration/activity.

Preparation of PDE7A/B Enzyme

PDE7 stock enzyme was prepared and kept at −20° C. in appropriately sized aliquots to reduce the number of freeze/thaw cycles. Table 3 below shows the volumes required to make 9 ml of PDE7A/B enzyme solution. PDE7A is diluted to 1/8000 and PDE7B to 1/10000.

TABLE 3

| Enzyme | Dilution | Vol. of PDE7 stock/diluted soln (µl) | Vol. of Buffer + BSA (µl) | Overall Dilution of Enzyme stock |
|---|---|---|---|---|
| PDE7A | PDE7B 1:100 dilution of stock | 5 | 495 | 1:100 |
| | 1:40 dilution of above solution | 25 | 975 | 1:4000 |
| | This enzyme solution is further diluted when all the assay components are dispensed into the assay plate i.e. 14 µl enzyme solution is dispensed into a total assay volume of 30 µl, giving an overall 1/8000-enzyme dilution. | | | |
| PDE7B | PDE7B 1:100 dilution of stock | 5 | 495 | 1:100 |
| | 1:50 dilution of above solution | 20 | 980 | 1:5000 |
| | This enzyme solution is further diluted when all the assay components are dispensed into the assay plate i.e. 14 µl enzyme solution is dispensed into a total assay volume of 30 µl, giving an overall 1/10000-enzyme dilution. | | | |

Once the enzyme solution was prepared it was kept on ice prior to usage.

Preparation of 50 nM Adenosine 3',5'Cyclic Phosphate (cAMP) Substrate Solution

The substrate is composed of a mixture of unlabelled cAMP and cAMP radiolabelled with tritium ([$^3$H]-cAMP). The specifications of the stock of [$^3$H]-cAMP will determine the volumes used.

The preparation of 9 ml of substrate solution using a [$^3$H]-cAMP stock which is 1 mCi/ml and 24 Ci/mmol (therefore 41.66 µM) is described below:

$K_m$ for the enzymes batches to date is as follows:
PDE7A—20 nM PDE7B—100 nM

The assay requires 15 µl of substrate solution to be dispensed into a total assay volume of 30 µl, ie a ×2 dilution in the assay plate occurs.

The final assay [cAMP] of ~25 nM is required, so ~50 nM [$^3$H]-cAMP was prepared.

9 ml of substrate solution was prepared by mixing 10.8 µl of [$^3$H]-cAMP (available from Amersham) with 8975 µl of assay buffer.

The exact concentration of cAMP was determined by taking 3 samples of 15 µl into scintillation vials. 4 m Starscint® (a scintillation cocktail, available from Perkin Elmer), was then added and the tubes counted on a β-counter on a dpm program.

The concentration of radioligand is determined by the following equation:

$$[\text{Radioligand}](M) = \frac{DPM}{(2.22 \times 10^{12}) \times \underset{\text{of radioligand}}{\text{(specific activity)}} \times \underset{\text{counted}}{\text{(volume of sample)}}}{(dpm/Ci)} \times \underset{(Ci/\text{Mol})}{} \times \underset{(L)}{}$$

The concentration is then divided by 2 to allow for the ×2 dilution occurring in the assay plate.

Preparation of 6.6 mg/ml Yttrium Silicate PDE SPA Beads

Phosphodiesterase SPA beads (Yttrium Silicate) are available from Amersham.

Following the manufacturer's recommendations the vial of beads was reconstituted using 28 ml distilled or deionised water (~20 mg/ml). The reconstituted beads are stable for 1 month when stored at 2-8° C. To prepare the beads for the assay, the reconstituted beads were diluted 3-fold in sterile double distilled water (~6.6 mg/ml). The beads can settle, so were constantly stirred/agitated whilst dispensing.

30 µl of the ~6.6 mg/ml beads are added to the 30 µl assay, giving a final bead concentration of ~0.2 mg/well.

Compound dilutions and "background" wells were made 30 stronger than required in the assay plate to allow for 1 µl compound to be diluted by 29 µl of other assay components (14 µl enzyme and 15 µl radioligand). Thus for a final assay concentration of 10 µM, the compound must be at 300 µM in the compound addition plate. 4 mM stocks of compound are supplied in 100% DMSO (or are made up @ 4 mM from powder submissions). This requires 1/13.33 dilution in DMSO to be made.

Assay Protocol

1 µl test compound was transferred into a suitable multi-well assay plate immediately prior to reagent assay addition, 14 µl enzyme solution was then added to the assay plate, followed by 15 µl substrate solution (ie: final assay volume 30 µl, with a final screening compound concentration of 1 µM). The plate was then sealed using a plate sealer and incubated at room temperature for 45 min on the plate shaker.

30 μl Yttrium Silicate PDE4 SPA beads were then added, ensuring constant stirring of the beads to give even distribution in the assay plate. The plate was then sealed using a plate sealer and incubated at room temperature for 30 mins on the plate shaker. The beads were then allowed to settle for 30 mins, before spinning the plates for 1 min at 200 g.

The plates were then read on a suitable radioactive counter, for example NXT-TopCount™ (available from Perkin Elmer) using the relevant protocol (30 second read time per well).

The data was fitted to a sigmoid curve using a least squares algorithm.

The $IC_{50}$ value was converted to a $K^i$ value using the Cheng-Prussof equation:

$$K_i = \frac{IC_{50}}{1 + \frac{[\text{radioligand}]}{K_m}}$$

The PDE7 inhibitory activity of the compounds of Examples 1-7 was tested according to the above protocol. The $K_i$ values obtained are shown in Table 4 below:

TABLE 4

| Example No | $K_i$ PDE7A (nM) | $K_i$ PDE7B (nM) |
|---|---|---|
| 1 | 1.9 | 4.6 |
| 2 | 3.1 | 13.4 |
| 3 | 15.6 | 108 |
| 4 | 11.6 | 144 |
| 5 | 276 | 1420 |
| 6 | NT | 17.6 |
| 7 | 19.8 | 140 |

NT = Not tested

Human Hepatocyte Data Summary

The human hepatic metabolic stability of the compounds of Examples 1-7 of the present application were assessed in the model described below. The compound of Example 75 of WO 02/074754, 5'-carboxypropoxy-8'-chloro-spiro[cyclohexane-1-4'-(3',4'-dihydro)quinazolin]-2'(1'H)-one (hereinafter "Compound A"), which is believed to represent the closest state of the art, was used as a comparison.

Method

Hepatocytes are used as an in vitro system to monitor hepatic metabolism as these intact cells contain all the hepatic enzymes found in vivo, including phase I enzymes, such as cytochrome P450 oxidases (CYPs), aldehyde oxidases and monoamine oxidases (MAOs), and phase 11 enzymes, such as UDP-glucuronyltransferases and sulfotransferases. Cryopreserved human hepatocytes are prepared from 5 donors and suspended in Williams' E media. 4-(2-hydroxyethyl)-1-piperazineethanesulfonic acid (HEPES) is added to a final concentration of 50 mM and pH is adjusted to 7.4. Test substrates are dissolved in DMSO are added to the hepatocytes to give a substrate concentration of 1 μM, with a final DMSO concentration in the incubation below 0.1%. The experiments are performed in 96 or 384 well plates at 37° C., with a hepatocyte density of 0.5 million viable cells/mL. Sampling times of 10, 20, 30, 60, 90, and 120 minutes are used and analytical quantitation is by LC-MS/MS. The intrinsic clearance (apparent) is calculated using the formula:

$CLint, app$=[−slope/0.5 M cells/mL]·1000 μL/mL=μL/min/M cells.

The human hepatic metabolic stability of the compounds of the present invention was tested according to the above protocol. The intrinsic clearance values obtained are shown in Table 5 below:

TABLE 5

| Compound | Human Hepatocytes CLint (μL/min/M cells) |
|---|---|
| Compound A | 25 |
| Example 1 | <5 |
| Example 2 | <5 |
| Example 3 | <5 |
| Example 4 | <5 |
| Example 5 | <5 |
| Example 6 | <5 |
| Example 7 | <5 |

The data presented in Table 5 above shows a clear differentiation, with respect to intrinsic hepatic metabolic stability, between the compounds of Examples 1-7 of the present application and the closest prior art, Compound A. It is therefore likely, based on the above data, that the reduced hepatic clearance of the compounds of Examples 1-7 of the present application will result in the compounds exhibiting improved half-life in humans, compared with Compound A.

Rat IV Pharmacokinetics Summary

The pharmacokinetic properties of the compounds of Examples 1 and 2 were tested in the rat model described below. The compound of Example 75 of WO 02/074754, 5'-carboxypropoxy-8'-chloro-spiro[cyclohexane-1-4'-(3',4'-dihydro)quinazolin]-2'(1'H)-one (hereinafter "Compound A"), which is believed to represent the closest state of the art, was used as a comparison.

Method

The test compounds were administered to male rats (each rat receiving one compound), via the tail vein, at a dose of 1 mg/kg (0.08 mg/kg for the compound of Example 1). Blood samples were withdrawn from the rats via a surgically implanted jugular vein cannula at predetermined time-points after administration, and centrifuged to produce plasma. Plasma samples were analysed via a specific LC-MS/MS assay for the quantification of drug in plasma. The resulting plasma concentration-time curves were interrogated using a non-compartmental pharmacokinetic analysis in order to understand the disposition of each compound. The resulting output was subsequently used to estimate the likely human pharmacokinetic profile, as described below.

The mean, dose normalised, pharmacokinetic profiles of the compounds of Examples 1 and 2, as well as that of Compound A, following 1 mg/kg intravenous administration are shown in Table 6 below and in FIG. 1.

TABLE 6

|  | Example 1 | Example 2 | Compound A |
|---|---|---|---|
| Cl (ml/min/kg) | 1.9 | 0.7 | 7 |
| fup | 0.07 | 0.1 | 0.045 |
| $Cl_u$ (ml/min/kg) | 27 | 70 | 156 |
| $V_d$ (ml/min/kg) | 0.6 | 0.7 | 0.4 |
| $T_{1/2}$ (hours) | 4 | 11 | <1 |

In Table 6, the following abbreviations are used:
Cl is the rat clearance;
$T_{1/2}$ is the half life;
$V_d$ is the volume of distribution in rat;
fup is the fraction unbound in rat plasma; and
$Cl_u$ is the unbound rat plasma clearance, where $Cl_u$ = Cl/fup.

Estimate of Human Pharmacokinetics

Based on the above pharmacokinetic data in the rat, the likely human pharmacokinetics of the compounds of Examples 1 and 2, and that of Compound A, can be estimated as follows.

Scaling the unbound rat plasma clearance ($Cl_{u\ rat}$) observed following intravenous administration to estimate an unbound human plasma clearance ($Cl_{u\ man}$) using the following relationship:

$$Cl_{u\ man} = Cl_{u\ rat} * (BW_{man}/BW_{rat})^{0.75}$$

where $BW_{man}$ & $BW_{rat}$ are the average body weights of man (70 kg) and rat (0.25 kg) respectively, and units of clearance are in ml/min.

Converting $Cl_{u\ man}$ to estimate total blood clearance in man ($Cl_{man}$):

$$Cl_{man} = [(Cl_{u\ man}) * f_{up}]/B{:}P$$

where $f_{up}$ is the free fraction of unbound drug in plasma and B:P is the blood to plasma ratio in human blood.

An estimate of human half-life is presented for each compound, derived using the relationship:

$$T_{1/2} = [ln(2) * V_d]/Cl$$

where $T_{1/2}$ is the estimated human half-life in hours, Vd is the volume of distribution in man (assumed to be 0.2 L/kg, due to the physicochemistry of this series) and Cl is the human clearance.

A summary of the estimated human pharmacokinetics is given in Table 7 below.

TABLE 7

|  | Example 1 | Example 2 | Compound A |
|---|---|---|---|
| $Cl_{u\ rat}$ (ml/min/kg) | 27 | 70 | 156 |
| fup | 0.07 | 0.01 | 0.03 |
| $Cl_{u\ man}$ (ml/min/kg) | 0.8 | 0.2 | 1.9 |
| B:P | 0.6 | 0.7 | 0.6 |
| Estimated $T_{1/2}$ (hours) | 3 | 10 | 1 |

The data presented in Tables 6 and 7 above show a clear differentiation, with respect to both the observed pharmacokinetics in the rat and the predicted human pharmacokinetics, between the compound of Example 2 of the present application when compared with the closest prior art Compound A. This is manifested in the projected human half-life which is estimated as 10 hours for the compound of Example 2, compared with Compound A which is likely to offer a half-life in man of approximately 1 hour.

It is therefore likely, based on the above data, that the pharmacokinetics of the compound of Example 2 of the present application will be commensurate with once or twice daily dosing in the clinic. The pharmacokinetics of the compound of Example 1 of the present application may be commensurate with twice or three times daily dosing. This represents a significant improvement over the closest prior art Compound A, which due to its short half-life is unlikely to be suitable for administration in a similar manner.

The activity of a compound of formula (I) according to the present invention in the treatment of neuropathic pain may be measured according to the following test protocol.

Animals: Male Sprague Dawley rats (average weight 500 g) are housed in groups of 12. All animals are kept under a 12 h light/dark cycle (lights on at 07 h 00 min) with food and water ad libitum. All experiments are carried out by an observer blind to the treatments and in accordance with the Home Office Animals (Scientific Procedures) Act 1986.

Chronic Constriction Injury (CCI) Rat Model of Neuropathic Pain

The CCI of sciatic nerve is performed as previously described (G. J. Bennett and Y. K. Xie, *Pain* (1988) 33, 87-107). Animals were anaesthetised with a 2% isofluorane/$O_2$ mixture. The right hind thigh is shaved and swabbed with 1% iodine. Animals are then transferred to a homeothermic blanket for the duration of the procedure and anaesthesia maintained during surgery via a nose cone. The skin is cut along the line of the thighbone. The common sciatic nerve is exposed at the middle of the thigh by blunt dissection through biceps femoris. About 7 mm of nerve is freed proximal to the sciatic trifurcation, by inserting forceps under the nerve and the nerve gently lifted out of the thigh. Suture is pulled under the nerve using forceps and tied in a simple knot until slight resistance is felt and then double knotted. The procedure is repeated until 4 ligatures (4-0 silk) are tied loosely around the nerve with approx 1 mm spacing. The incision is closed in layers and the wound treated with topical antibiotics.

Streptozocin (STZ)-induced Diabetes Neuropathy in the Rat

Diabetes is induced by a single intraperitoneal injection of streptozotocin (50 mg/kg) freshly dissolved in 0.9% sterile saline. Streptozotocin injection induces a reproducible mechanical allodynia within 3 weeks, lasting for at least 7 weeks (S. R. Chen and H. L. Pan. *J. Neurophysiol.* (2002), 87, 2726-2733).

Assessment of Static and Dynamic Allodynia

Static Allodynia

Animals are habituated to wire bottom test cages prior to the assessment of allodynia. Static allodynia is evaluated by application of von Frey hairs (Stoelting, Wood Dale, Ill., USA) in ascending order of force (0.6, 1, 1.4, 2, 4, 6, 8, 10, 15 and 26 grams) to the plantar surface of hind paws. Each von Frey hair is applied to the paw for a maximum of 6 seconds, or until a withdrawal response occurs. Once a withdrawal response to a von Frey hair is established, the paw is re-tested, starting with the filament below the one that produced a withdrawal, and subsequently with the remaining filaments in descending force sequence until no withdrawal occurred. The highest force of 26 g lifts the paw as well as eliciting a response, thus representing the cut off point. Each animal has both hind paws tested in this manner. The lowest amount of force required to elicit a response is recorded as paw withdrawal threshold (PWT) in grams. Static allodynia is defined as present if animals responded to a stimulus of, or less than, 4 g, which is innocuous in naive rats (M. J. Field et al. *Pain* (1999), 83, 303-11).

Dynamic Allodynia

Dynamic allodynia is assessed by lightly stroking the plantar surface of the hind paw with a cotton bud. To avoid recording general motor activity, care is taken to perform this procedure in fully habituated rats that were not active. At least two measurements are taken at each time point, the mean of which represents the paw withdrawal latency (PWL). If no reaction is exhibited within 15 sec the procedure is terminated and animals are assigned this withdrawal time. A pain withdrawal response is often accompanied with repeated flinching or licking of the paw. Dynamic allodynia is considered to be present if animals respond to the cotton stimulus within 8 seconds of commencing stroking (Field et al, 1999, above).

EXAMPLES $^1$H Nuclear magnetic resonance (NMR) spectra were in all cases consistent with the proposed structures. Characteristic chemical shifts (δ) are given in parts per million (ppm) downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionisation (ES or ESI) or atmospheric pressure chemical ionisation (APCI). The following abbreviations have been used for common solvents: CDCl$_3$, deuterochloroform; D$_6$-DMSO, hexadeuterodimethylsulphoxide.

Single Crystal X-Ray Diffraction Experimental

The crystal structure of the acetic acid solvate of the compound of Example 2 was determined by Single Crystal X-Ray diffraction at room temperature using a Bruker SMART APEX Single Crystal X-Ray diffractometer and Mo Kα radiation. Intensities were integrated using SMART v5.622 (control) and SAINT v6.02 (integration) software (Bruker AXS Inc., Madison, Wis., USA, 1994) from several series of exposures where each exposure covered 0.30° in ω, with an exposure time of 60 s and the total data set was more than a hemisphere. Data were corrected for absorption using the multiscans method (SADABS, Program for scaling and correction of area detector data, G. M. Sheldrick, University of Göttingen, 1997, based on the method of R. H. Blessing, *Acta Cryst.* 1995, A51, 33-38).

The crystal structure was successfully solved by direct methods using SHELXS-97, (Program for crystal structure solution. G. M. Sheldrick, University of Göttingen, Germany, 1997, release 97-2) in Space Group C2/c and refined by the method of least-squares using SHELXL-97 (Program for crystal structure refinement. G. M. Sheldrick, University of Göttingen, Germany, 1997, release 97-2). The crystal structure refinement procedure revealed the presence of a molecule of the compound of Example 2 and a molecule of acetic acid within the asymmetric unit. Hence this structure can be termed a 1:1 acetic acid solvate of the compound of Example 2.

Calculation of the Powder X-Ray Diffraction Pattern from the Example 2, Step (b) (Acetic Acid Solvate) Crystal Structure 2θ angles and relative intensities (see Table 8 below) were calculated from the single crystal structure of the acetic acid solvate of the compound of Example 2 using the "Reflex Powder Diffraction" module of Accelrys MS Modelling™ [version 3.0]. Pertinent simulation parameters were:

Wavelength=1.5406 Å (Cu Kα)
Polarisation Factor=0.5
Pseudo-Voigt Profile (U=0.01, V=−0.001, W=0.002)

Figure 2:
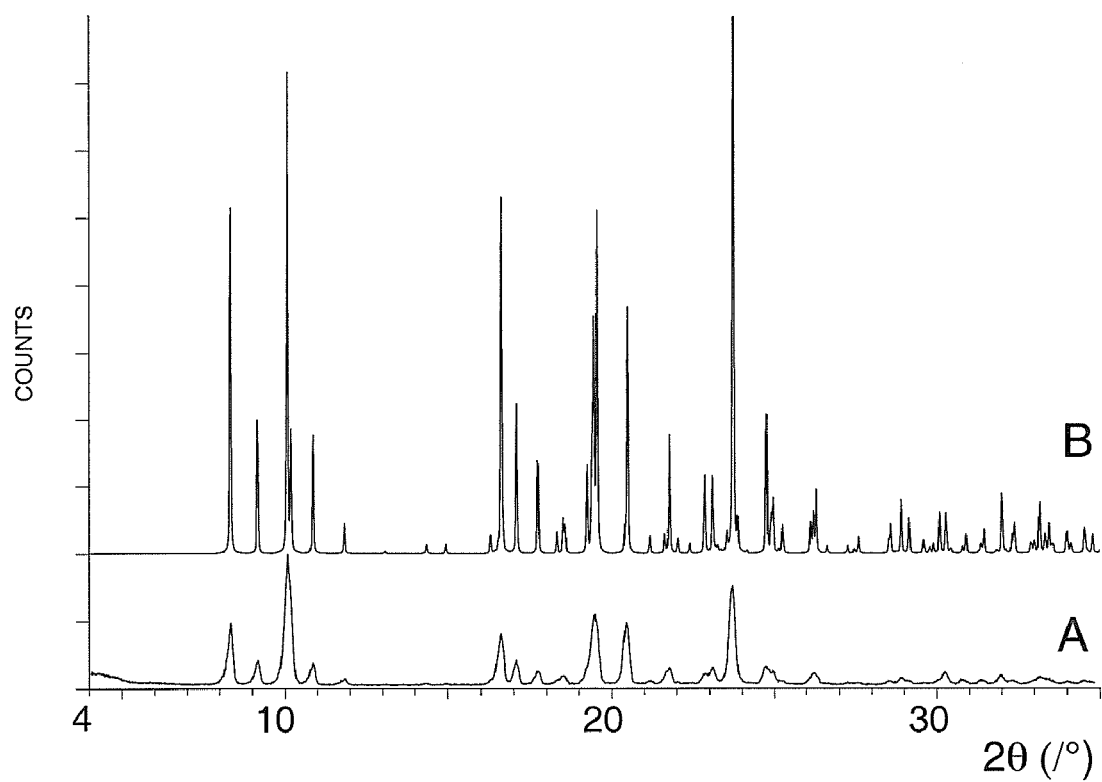
FIG. 2 shows powder X-ray diffraction (PXRD) plots for measured (A) and simulated (B) patterns for the acetic acid solvate of the compound of Example 2.

The calculated pattern represents that of a pure phase of the acetic acid solvate of the compound of Example 2 since it is derived from a single crystal structure. A comparison of the measured and calculated patterns is shown in FIG. 2 and demonstrates that the bulk is represented by the single crystal structure. Slight discrepancies between peak intensities can be attributed to preferred orientation effects is the measured pattern.

Powder X-Ray Diffraction

The powder X-ray diffraction pattern for the unsolvated crystalline form of the compound of Example 2 (Form A) was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by initially doping with silicon, in order to measure accurate peak positions, and was subsequently mounted on a low background silicon wafer specimen mount. The specimen was rotated whilst being irradiated with copper K-alpha$_1$ X-rays (wavelength=1.5406 Ångstroms) with the X-ray tube operated at 40 kV/30 mA. The analyses were performed with the goniometer running in continuous mode set for a 0.2 second count per 0.018° step over a two theta range of 2° to 55°. The PXRD patterns for the vacuum dried solvate samples were also collected using the same parameters on this diffractometer, but these samples were not doped with silicon.

All other powder X-ray diffraction patterns were recorded for samples mounted on a flat silicon wafer, using a Bruker AXS Ltd. D8 Advance powder X-ray diffractometer fitted with Gobel mirror optics, a single sample stage and a position sensitive detector (PSD). Each specimen was irradiated with copper K-alpha$_1$ X-rays (wavelength=1.5406 Å) with the X-ray tube operated at 40 kV/40 mA. The analyses were performed with the goniometer running in continuous scan mode set for a 0.2 second count per 0.014° step over a range of 3° to 35° 2θ.

Differential Scanning Calorimetry (DSC)

DSC measurements were made using a Perkin Elmer Diamond Differential Scanning Calorimeter. The sample was heated at 20° C./minute, from ambient to 300° C., in a 50 μl vented aluminium pan. Flow gas was nitrogen at 40 ml/min.

Themogravimetric Analysis (TGA)

TGA measurements of the solvates were made using TA Instruments TGA2950 Hi-Res Thermogravimetric Analyser using nitrogen purge gas at a rate of 75 cm$^3$/min from ambient to the desolvation temperature (150° C.-180° C.) at a heating rate of 20° C./min. The sample was then cooled to room temperature for subsequent PXRD analysis.

Example 1

Cis-3-[(8'-chloro-2'-oxo-2',3'-dihydro-1'H-spiro[cyclohexane-1,4'-quinazolin]-5'-yl)oxy]cyclobutanecarboxylic acid

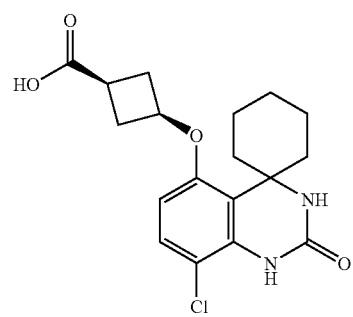

To a solution of the alcohol of Preparation 8 (50 mg, 0.14 mmol) in 99.25:0.75 acetonitrile:water (2 ml) was added a solution of periodic acid (82 mg, 0.359 mmol) and chromium (VI) oxide (1.6 mg, 0.016 mmol) in 99.25:0.75 acetonitrile:water (2 ml), maintaining the reaction temperature below 5° C.

The reaction mixture was stirred at room temperature for 18 hours. The reaction mixture was filtered and the residue washed with 99.25:0.75 acetonitrile:water, 2N hydrochloric acid:methanol (5:1), water and methanol. The residue was dried in vacuo to yield the title compound as a white solid (28 mg, 0.077 mmol, 55%).

$^1$H-NMR (400 MHz, D$_6$-DMSO): δ 1.17 (m, 1H), 1.40-1.65 (m, 5H), 1.79 (m, 2H), 2.16 (m, 2H), 2.48 (m, 2H), 2.72 (m, 3H), 4.64 (m, 1H), 6.43 (d, 1H), 7.0 (s, 1H), 7.21 (d, 1H), 7.90 (s, 1H), 12.26 (bs, 1H).

LRMS m/z (APCI): 365[M+H]$^+$, 406[M+CH$_3$CN+H]$^+$

Example 2

Trans-3-[(8'-chloro-2'-oxo-2',3'-dihydro-1'H-spiro[cyclohexane-1,4'-quinazolin]-5'-yl)oxyl cyclobutanecarboxylic acid

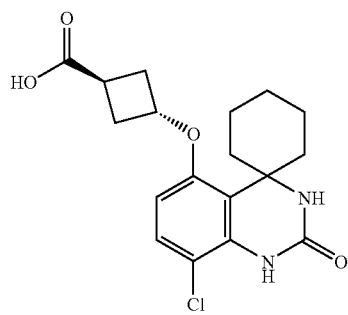

Method A

To a solution of the alcohol of Preparation 11 (2.05 g, 5.84 mmol) in acetonitrile containing 0.75% water (50 ml) was added a solution of chromium (VI) oxide (12 mg, 0.11 mmol) and periodic acid (3.33 g, 14.6 mmol) and the reaction mixture stirred at 40° C. for 96 hours. Water (100 ml) was added and the suspension stirred for 2 hours. The resulting precipitate was collected by filtration, washed with water and dried in vacuo to yield the title compound (1.90 g, 5.2 mmol, 89%).

$^1$H-NMR (400 MHz, D$_6$-DMSO): δ 1.2 (m, 1H), 1.2 (m, 2H), 1.6 (m, 2H), 1.8 (m, 2H), 2.3 (m, 2H), 2.6 (m, 2H), 3.1 (m, 1H), 3.2 (s, 1H), 4.0 (bs, 1H), 4.8 (m, 1H), 6.4 (d, 1H), 7.0 (s, 1H), 7.2 (d, 1H), 7.9 (s, 1H).

LRMS m/z (APCI) 365 [MH]$^+$

Method B

Step (a)

Trans-3-[(8'-chloro-2'-oxo-2',3'-dihydro-1'H-spiro[cyclohexane-1,4'-quinazolin]-5'-yl)oxy]cyclobutanecarboxylic acid tert-butyl ester

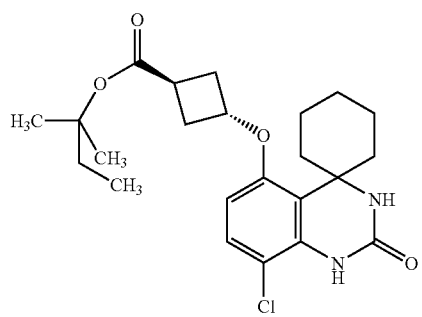

The compound of Preparation 27, step (b) (34.1 g, 130 mmol) was suspended in DMF (300 ml) and the slurry warmed to 35° C. Cesium carbonate (63 g, 190 mmol) was added in one portion. The compound of Preparation 22 was dissolved in DMF (90 ml) and added to the reaction. The reaction was heated to 90° C. over 1 hour and held for 8 hours. The reaction was cooled to 73° C. and water (160 ml) added whilst maintaining the temperature above 65° C. The resulting slurry was cooled to 35° C., following which ethyl acetate (260 ml) was added in one portion. After cooling to room temperature, the slurry was filtered and the product washed with ethyl acetate (2×100 ml). The resulting white solid was dried in vacuo at 60° C. for 16 hours to give the title compound as a white solid (44.4 g, 105 mmol, 82%).

$^1$H-NMR (300 MHz, CDCl$_3$): δ 1.3 (m, 1H), 1.4 (m, 1H), 1.5 (s, 9H), 1.6 (m, 1H), 1.7 (bm, 1H), 1.8 (bm, 2H), 1.8 (bm, 1H), 2.4 (m, 2H), 2.6 (t, 2H), 2.7 (m, 2H) 3.1 (m, 1H), 3.2 (m, 1H) 4.8 (m, 1H), 5.5 (s, 1H), 6.2 (d, 1H), 6.9 (s, 1H), 7.1 (d, 1H).

LC-MS (ESI): 22.6 minutes 11.8 (%) {cis isomer} m/z 422 [MH$^+$]; 23.1 minutes 88.2 (%) {trans isomer} m/z 422 [MH$^+$].

Step (b)

Trans-3-[(8'-chloro-2'-oxo-2',3'-dihydro-1'H-spiro[cyclohexane-1,4'-quinazolin]-5'-yl)oxy]cyclobutanecarboxylic acid acetic acid solvate

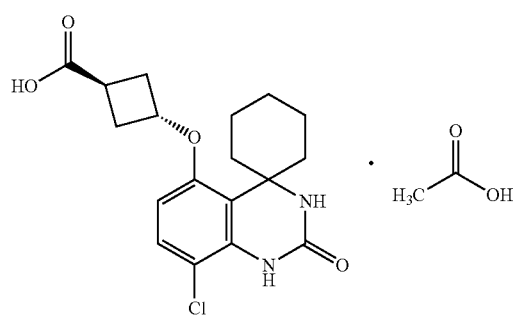

The product of step (a) (207 g, 0.492 mol) was slurried in acetic acid (3100 ml) and heated to 60° C. 48% Hydrobromic acid (4.93 mol) was added dropwise keeping the temperature at 60° C. The solution was stirred at 60° C. for 30 minutes. Water (700 ml) was added dropwise keeping the temperature above 55° C. The slurry was cooled to 20° C. and stirred for a further 30 minutes after which it was filtered, washed with acetic acid:water (2000 ml) and water (1000 ml) before being dried in a vacuum oven overnight at 60° C. to yield a white solid of the title compound as an acetic acid solvate (153.6 g, 73.5%).

$^1$H-NMR (400 MHz, D$_6$-DMSO): δ 1.2 (m, 1H), 1.2 (m, 2H), 1.6 (m, 2H), 1.8 (m, 2H), 1.9 (s, 3H, CH$_3$COOH), 2.3 (m, 2H), 2.6 (m, 2H), 3.1 (m, 1H), 3.2 (s, 1H), 4.0 (bs, 1H), 4.8 (m, 1H), 6.4 (d, 1H), 7.0 (s, 1H), 7.2 (d, 1H), 7.9 (s, 1H), 9.9 (s, 1H, CH$_3$COOH).

LC-MS (ESI): 18.0 minutes 1.65 (%) {cis isomer} m/z 365 [MH$^+$]; 18.3 minutes 98.4 (%) {trans isomer} m/z 365 [MH$^+$].

The above acetic acid solvate has been found to crystallise with a 1:1 stoichiometry, as shown from its crystal structure determined by the method of single crystal X-ray diffraction. FIG. 2 shows the measured powder X-ray diffraction (PXRD) pattern (A) for a batch of the above acetic acid solvate along with the simulated PXRD pattern (B) calculated from the single crystal structure. It can be seen that the peak positions for the two patterns agree very well. Any difference in relative intensity and width of the diffraction peaks can be attributed to preferred orientation and particle size effects respectively. The characteristic 2θ X-Ray diffraction peaks and their relative intensities for the above acetic acid solvate are listed in Table 8 below.

TABLE 8

| 2θ/° | Intensity % |
|---|---|
| 8.3 | 58.5 |
| 10.8 | 18.3 |
| 16.6 | 52.5 |
| 17.1 | 22.7 |
| 17.7 | 14.6 |
| 19.2 | 14 |
| 19.5 | 24.1 |
| 20.5 | 36.8 |
| 21.8 | 18.4 |
| 22.9 | 12.5 |
| 23.1 | 12.4 |
| 23.7 | 100 |
| 24.7 | 21.2 |
| 26.3 | 10.4 |

Figure 3:
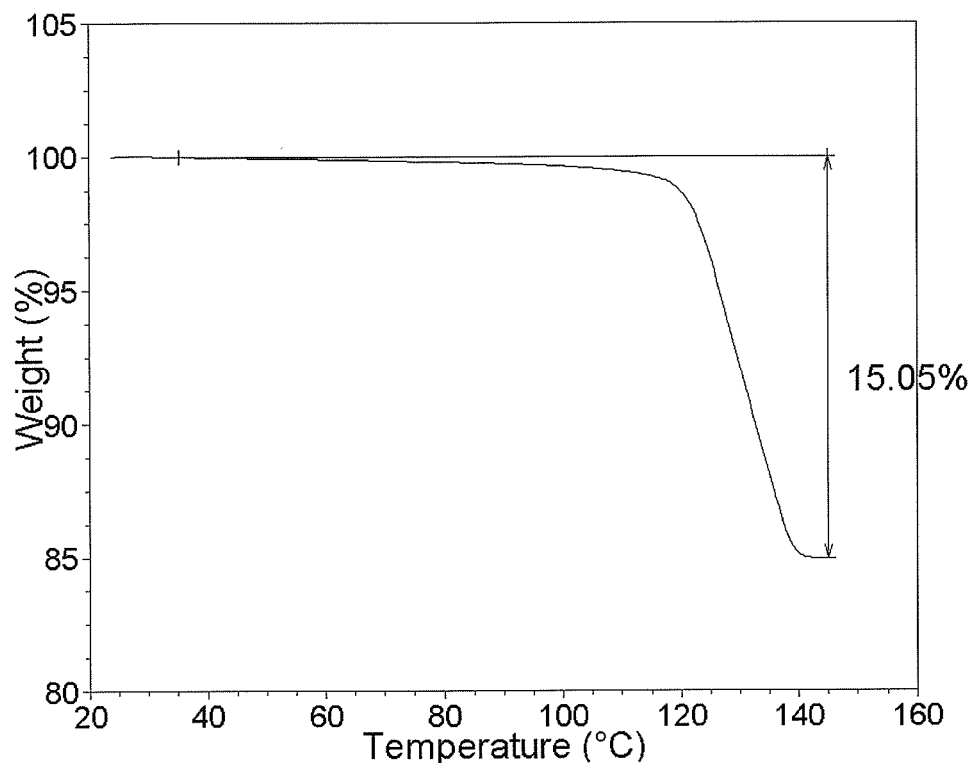
FIG. 3 is a plot of mass loss on heating using thermogravimetric analysis (TGA) on the acetic acid solvate of the compound of Example 2 (the 15.05% mass loss shown being equal to 1 mole equivalent of acetic acid)
Figure 4:
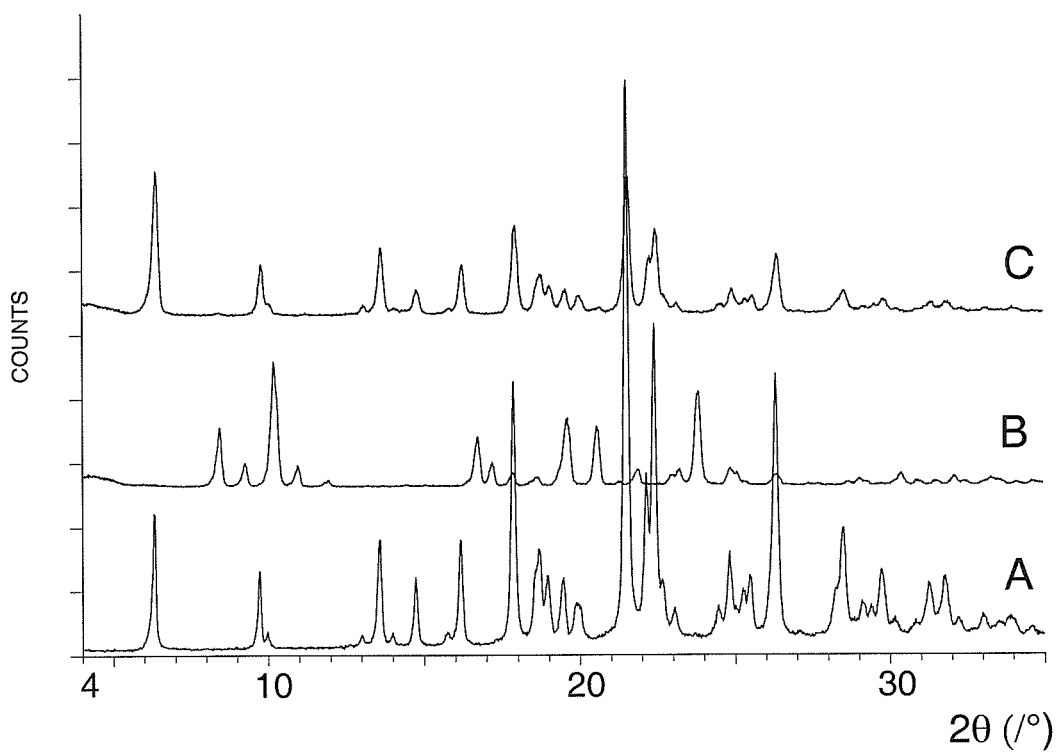
FIG. 4 shows PXRD patterns for the silicon-doped asolvated form (Form A) of the compound of Example 2 (A), and the acetic acid solvate of this compound before TGA (B) and after TGA analysis (C)

The acetic acid solvate has been found to thermally desolvate at around 115° C., as shown by Themogravimetric Analysis (TGA) where a sharp ~15% weight loss is observed at this temperature, which equates to the one mole equivalent of acetic acid. The TGA plot is shown in FIG. 3. Upon desolvation, the above solvate recrystallises to the desolvated Form A (described in step (c) below), as demonstrated by the PXRD plots shown in FIG. 4.

Step (c)

Trans-3-[(8'-chloro-2'-oxo-2',3'-dihydro-1'H-spiro [cyclohexane-1,4'-quinazolin]-5'-yl)oxy]cyclobutanecarboxylic acid The acetic acid solvate of step (b), (157 g, 369 mmol) was slurried in water (5200 ml) at room temperature overnight. The slurry was then filtered and washed with water (4×500 ml) before being dried in a vacuum oven overnight at 60° C. to yield the unsolvated title compound as a white solid (130 g, 357 mmol, 96%).

$^1$H-NMR (400 MHz, D$_6$-DMSO): δ 1.2 (m, 1H), 1.2 (m, 2H), 1.6 (m, 2H), 1.8 (m, 2H), 2.3 (m, 2H), 2.6 (m, 2H), 3.1 (m, 1H), 3.2 (s, 1H), 4.0 (bs, 1H), 4.8 (m, 1H), 6.4 (d, 1H), 7.0 (s, 1H), 7.2 (d, 1H), 7.9 (s, 1H).

LRMS m/z (APCI) 365 [MH]$^+$

Figure 5:
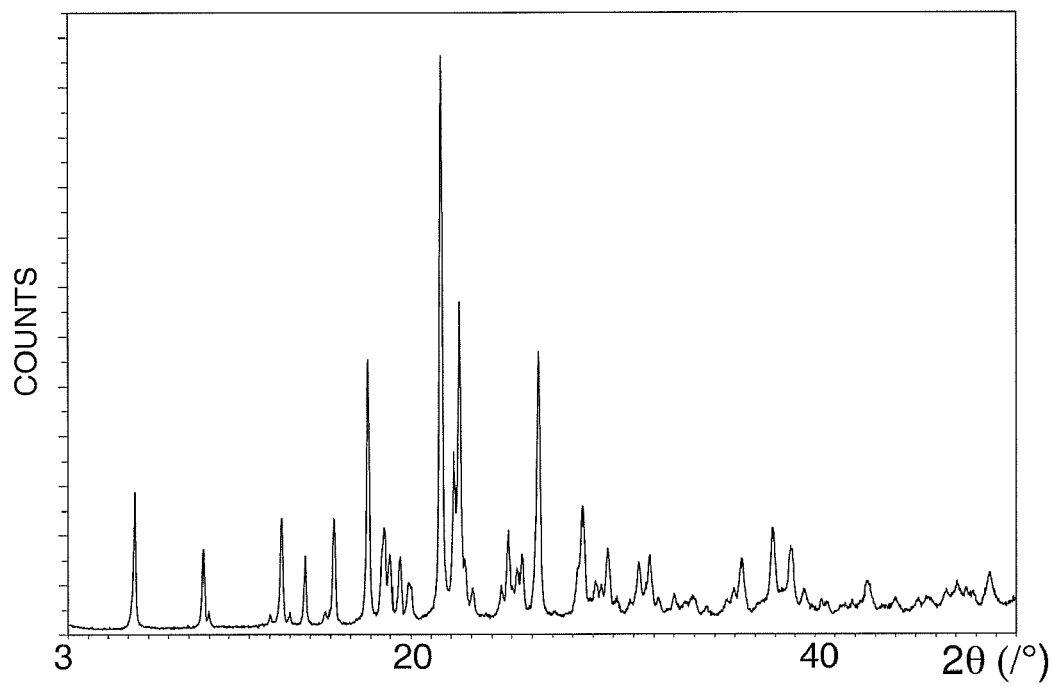
FIG. 5 shows the PXRD pattern of the unsolvated crystalline form (Form A) of the compound of Example 2, corrected relative to silicon standard.
Figure 6:
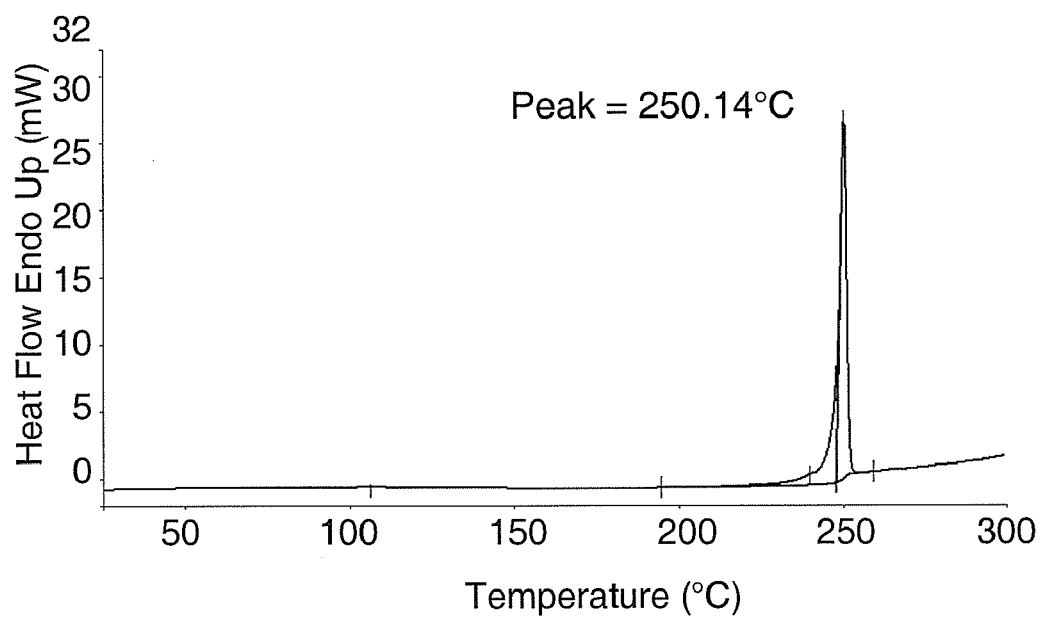
FIG. 6 is a differential scanning calorimetry (DSC) trace for of the unsolvated crystalline form (Form A) of the compound of Example 2.

This compound has also been found to crystallise in an unsolvated form (Form A) with a characteristic powder X-ray diffraction (PXRD) pattern shown in FIG. 5. The characteristic 2θ X-ray diffraction peaks and their relative intensities are listed in Table 9 below. This crystalline form has a melting point of 250° C. as determined by Differential Scanning Calorimetry (DSC) illustrated in FIG. 6.

TABLE 9

| 2θ/° | Intensity % |
|---|---|
| 6.3 | 24.6 |
| 9.7 | 14.6 |
| 13.6 | 20.0 |
| 14.7 | 13.4 |
| 16.2 | 20.0 |
| 17.8 | 47.5 |
| 18.5 | 15.9 |
| 18.7 | 18.3 |
| 18.9 | 13.7 |
| 19.4 | 12.9 |
| 21.5 | 100.0 |
| 22.1 | 31.5 |
| 22.4 | 57.5 |
| 22.7 | 13.0 |
| 24.8 | 17.9 |
| 25.3 | 11.3 |
| 25.5 | 13.7 |
| 26.3 | 48.8 |
| 28.2 | 11.2 |
| 28.5 | 22.0 |
| 29.8 | 14.7 |
| 31.3 | 12.1 |
| 31.8 | 13.5 |
| 36.4 | 12.8 |
| 37.9 | 18.2 |
| 38.8 | 15.2 |
| 48.7 | 10.4 |

Figure 7:
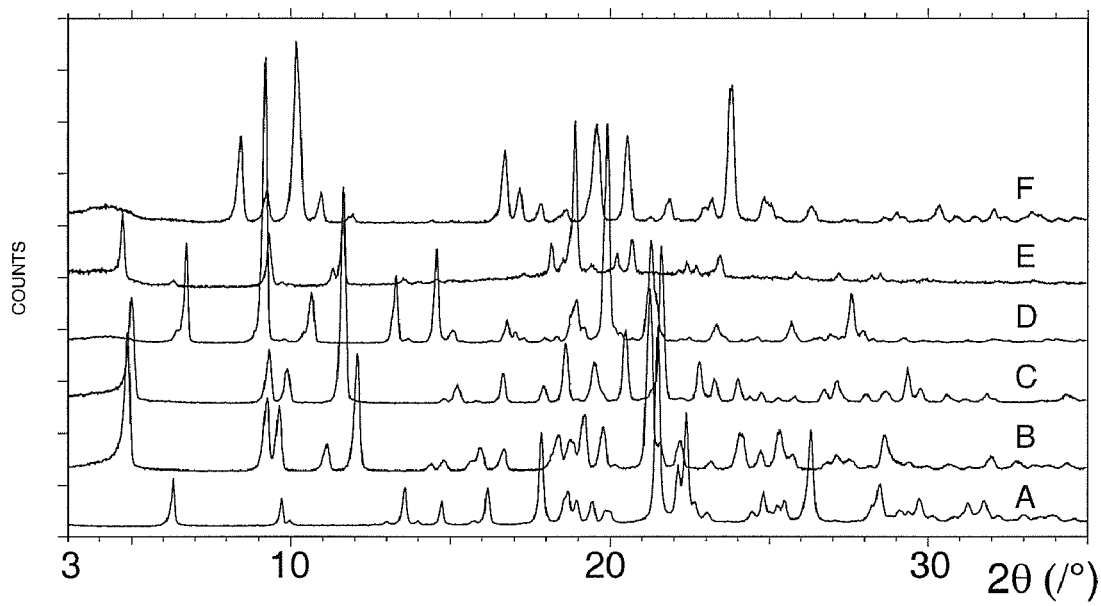
FIG. 7 shows PXRD plots for the crystalline unsolvated form (Form A) and the dimethylacetamide (DMAC) (B), pyridine (C), tetrahydrofuran (THF) (D), dimethylsulfoxide (DMSO) (E) and acetic acid (F) solvates of the compound of Example 2.

The compound of Example 2 has also been found to crystallise as solvates with dimethylacetamide (DMAC), pyridine, tetrahydrofuran (THF) and dimethylsulfoxide (DMSO). Each of these solvates has a characteristic PXRD pattern, as shown in FIG. 7.

Figure 8:
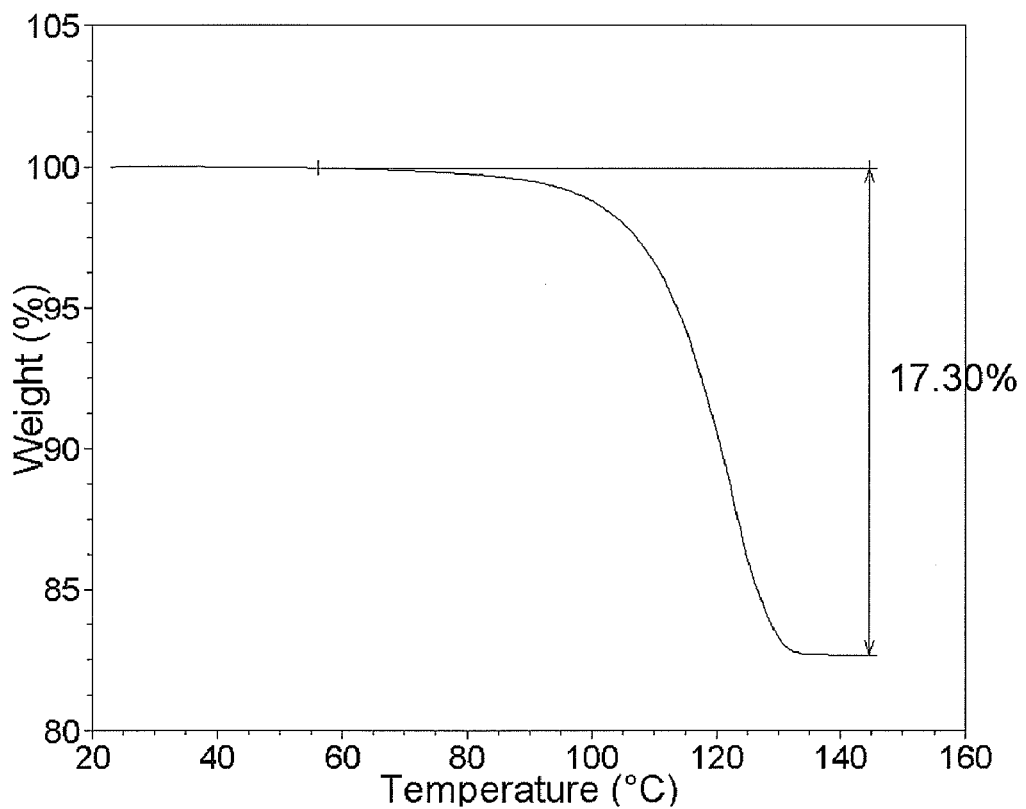
FIG. 8 is a TGA trace of the pyridine solvate of the compound of Example 2, the mass loss of 17.3% shown being equivalent to a 1:1 ratio of solvent to compound.
Figure 9:
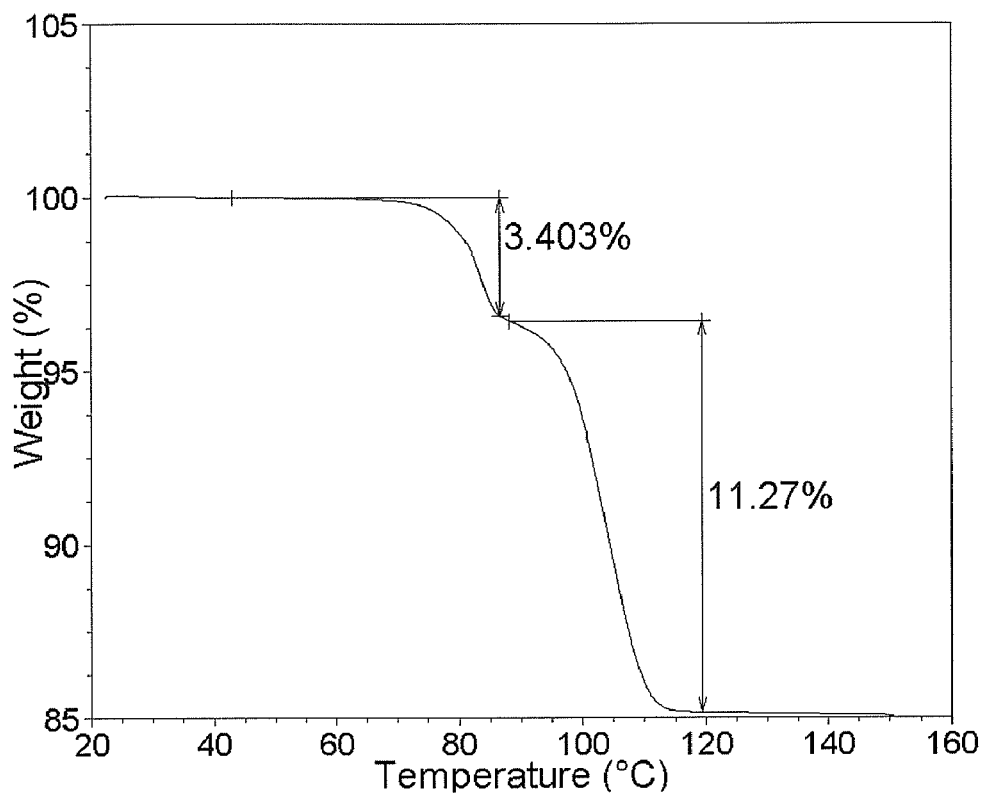
FIG. 9 is a TGA trace of the tetrahydrofuran solvate of the compound of Example 2, the total mass loss of 14.7% corresponding to a 1:1 ratio of compound to THF solvent (the stepwise nature of the solvent loss on heating possibly indicating the presence of an intermediate hemi-THF solvate form)
Figure 10:
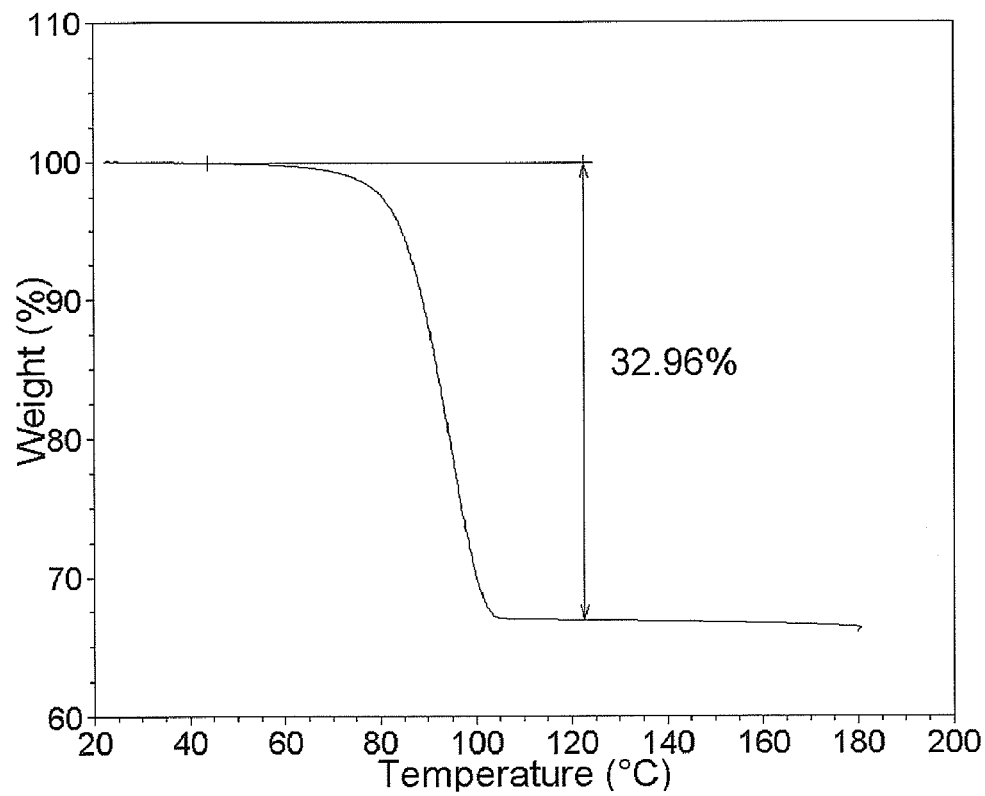
FIG. 10 is a TGA trace of the dimethylacetamide solvate of the compound of Example 2, the total mass loss of 33.0% being equivalent to a 2:1 ratio of solvent to compound.
Figure 11:
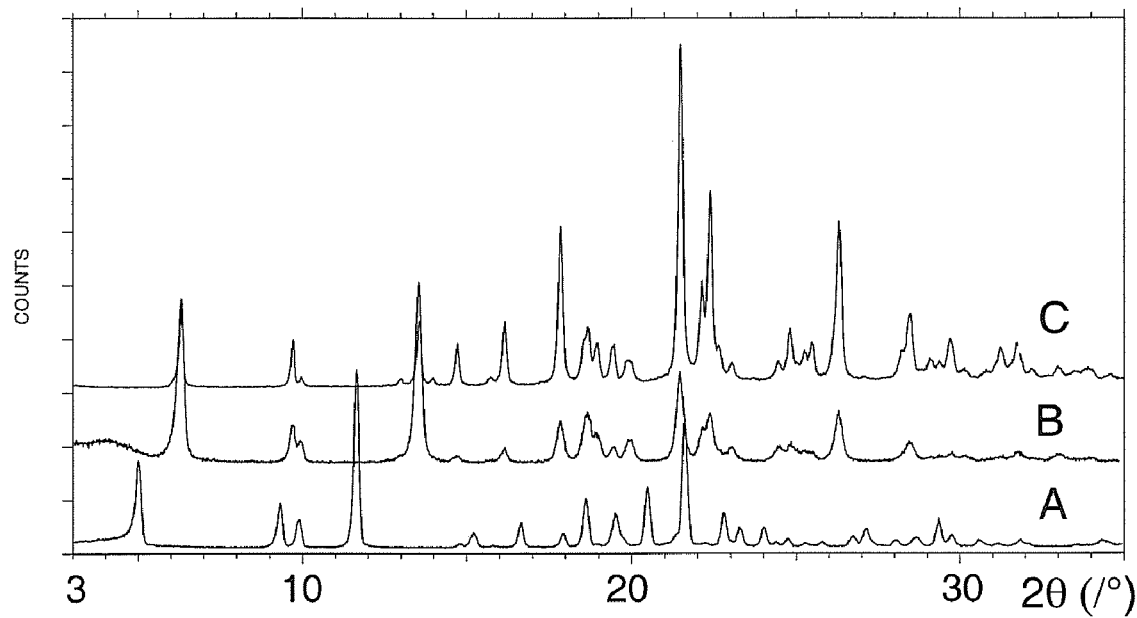
FIG. 11 shows PXRD patterns for the pyridine solvate (A), the pyridine solvate after TGA (B) and Form A (C) of the compound of Example 2.
Figure 12:
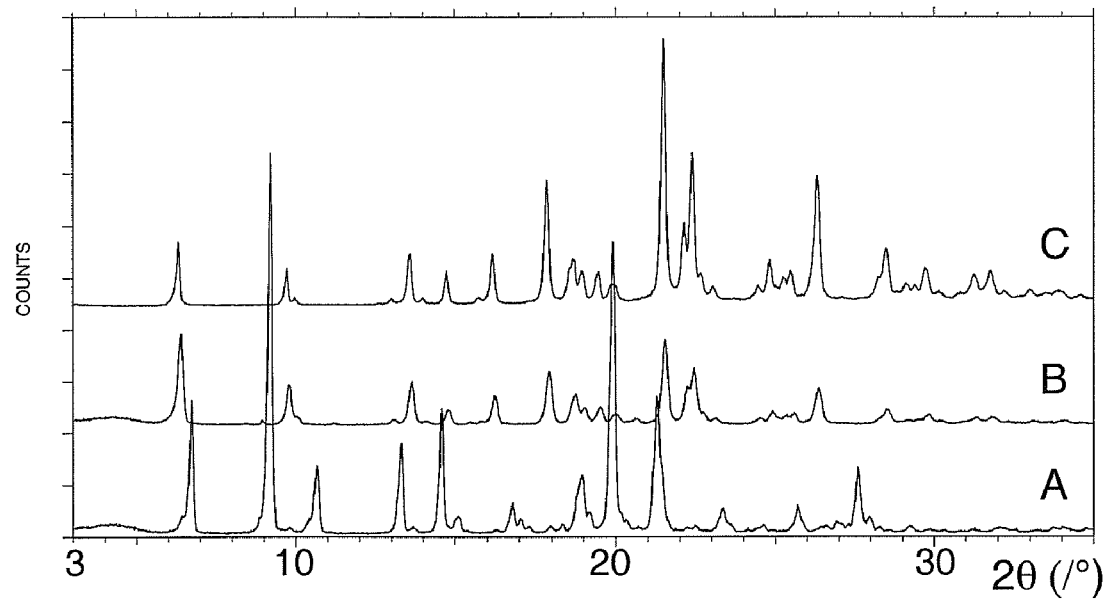
FIG. 12 shows PXRD patterns for the tetrahydrofuran solvate (A), the THF solvate after TGA (B) and Form A (C) of the compound of Example 2.
Figure 13:
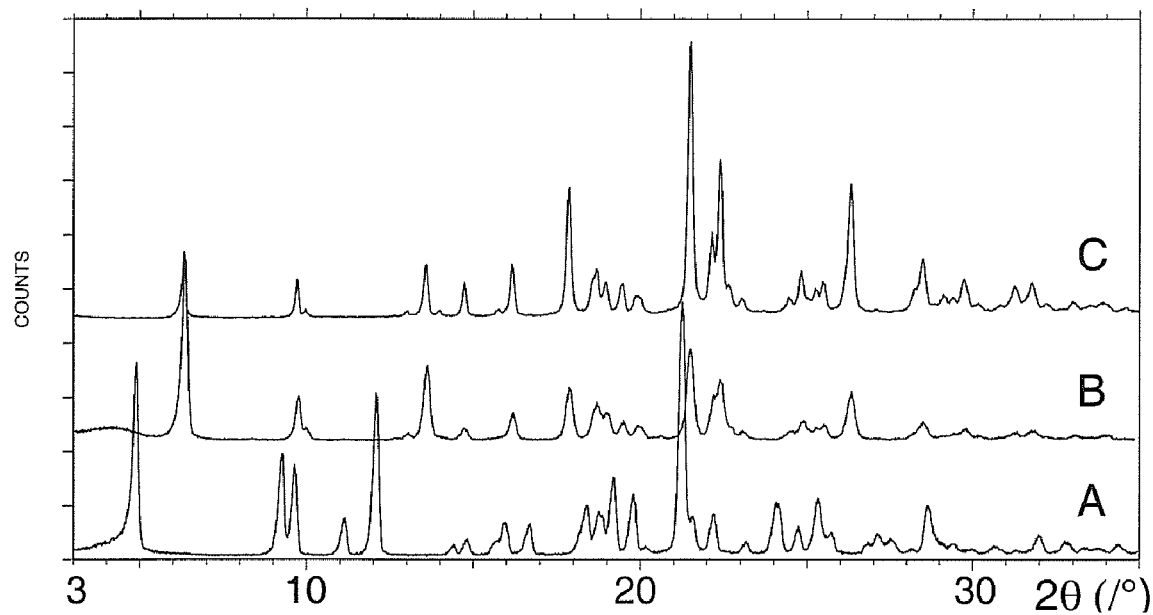
FIG. 13 shows PXRD patterns for the dimethylacetamide solvate (A), the dimethylacetamide solvate after TGA (B) and Form A (C) of the compound of Example 2.
Figure 14:
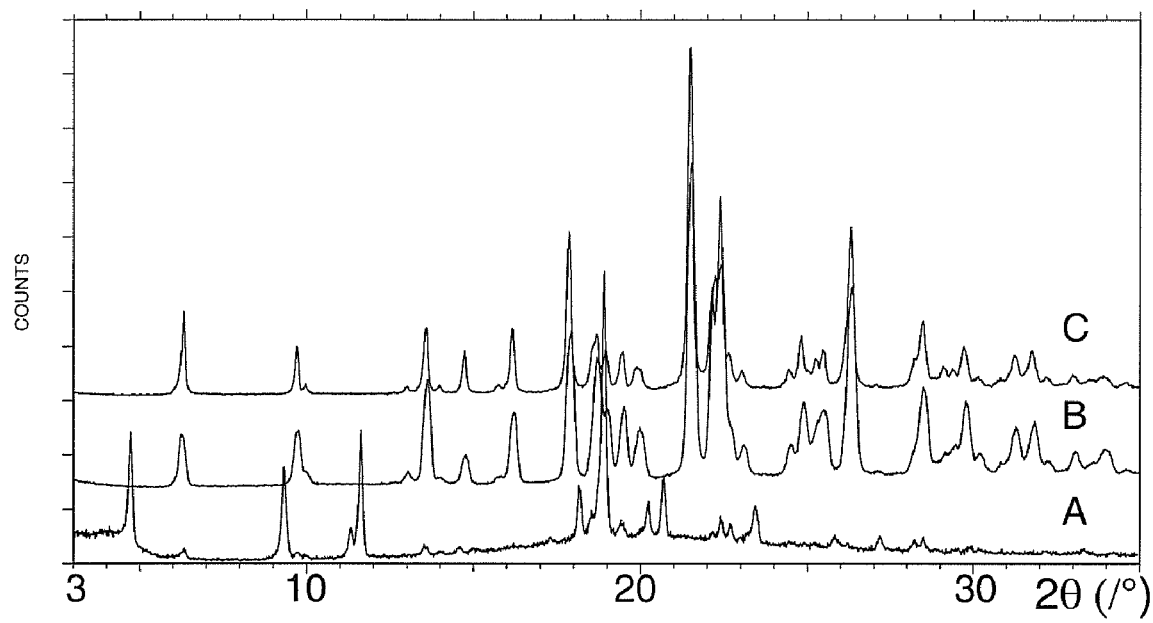
FIG. 14 shows PXRD patterns for the dimethylsulfoxide solvate (A), the DMSO solvate after vacuum drying (B) and Form A (C) of the compound of Example 2.

TGA measurements of these solvates have revealed the pyridine and THF solvates to have a 1:1 stoichiometry (FIGS. 8 & 9), while the DMAC solvate has been shown to have a 2:1 solvent to compound stoichiometry (FIG. 10). The fragile nature of the DMSO solvate has meant that its stoichiometry could not be determined.

Upon desolvation each of the pyridine, THF, DMAC and DMSO solvates recrystallises to the anhydrous Form A, as demonstrated by PXRD analysis shown in FIGS. 11, 12, 13 and 14 respectively.

Example 3

3-[(8'-fluoro-2'-oxo-2',3'-dihydro-1'H-spiro[cyclohexane-1,4'-quinazolin]-5'-yl)oxymethyl]cyclobutanecarboxylic acid

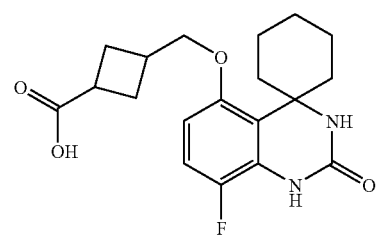

(a) 3-[(8'-chloro-2'-oxo-2',3'-dihydro-1'H-spiro[cyclohexane-1,4'-quinazolin]-5'-yl)oxymethyl]cyclobutanecarboxylic acid benzyl ester

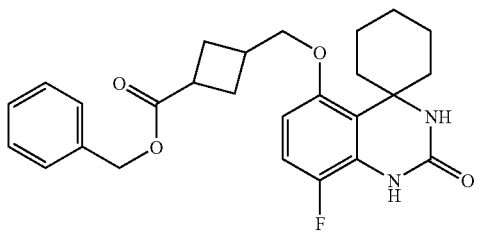

8'-fluoro-5'-hydroxy-1'H-spiro[cyclohexane-1,4'-quinazolin]-2'(3'H)-one (140 mg, 0.56 mmol) (prepared as described in WO 2004/026818, intermediate c) and caesium carbonate (301 mg, 0.925 mmol) were combined in DMF (2 ml), a solution of the compound of Preparation 15 (220 mg, 0.588 mmol) in DMF (2 ml) added and the mixture stirred at 80° C. for 18 hours. Water (35 ml) was then added and the product extracted with ethyl acetate (2×25 ml). The combined organic extracts were washed with saturated brine and dried over magnesium sulphate. Evaporation of the solvent afforded the title compound, a brown gum, as a ~5:4 mixture of cis and trans isomers (204 mg, 80%).

$^1$H-NMR (400 MHz, CDCl$_3$): δ 1.29 (m, 1H), 1.66 (m, 7H), 2.21 (m, 2H), 2.41 (m, 2H), 2.59 (m, 2H), 2.8 & 2.90 (2m, 1H), 3.2 (m, 1H), 3.96 & 4.00 (2×d, 2H), 5.13 (2×s, 2H), 6.6 (m, 1H), 6.95 (m, 1H), 7.33 (m, 5H).

LRMS m/z (ES) 453 [MH]$^+$ (b) 3-[(8'-fluoro-2'-oxo-2',3'-dihydro-1'H-spiro[cyclohexane-1,4'-quinazolin]-5'-yl)oxymethyl]cyclobutanecarboxylic acid The product of step (a) (200 mg, 0.442 mmol) was dissolved in methanol (2 ml), 2M NaOH (2 ml, 4.0 mmol) added and the brown emulsion stirred at 60° C. for 1.5 hours, before cooling. 2N HCl (2 ml, 4.0 mmol) was added and the resulting suspension stirred for 1.5 hours. The cream solid collected by filtration, washing well with water to yield the title compound (136 mg, 85%) after drying in vacuo.

Chiral HPLC on Chiralpak AD-H, 15% isopropanol:85% hexane+0.1% trifluoroacetic acid shows a 43:57 ratio of isomers (retention times 13.69 and 15.27 minutes).

$^1$H-NMR (400 MHz, CDCl$_3$): δ 1.16 (m, 1H), 1.43 (m, 2H), 1.57(m, 3H), 1.76 (m, 2H), 2.05 (m, 2H), 2.28 (m, 2H), 2.43 (m, 2H), 2.68 (2×m, 1H), 3.03 (2×m, 1H), 3.88 & 3.97 (2×d, 2H), 6.48 (m,1H), 6.76 (m, 1H), 6.98 (m, 1H), 8.79 (s, 1H), 12.06 (br, 1H).

LRMS m/z (ES) 363 [MH]$^+$

Example 4 trans-3-[(8'-cyano-2'-oxo-2',3'-dihydro-1'H-spiro[cyclohexane-1,4'-quinazolin]-5'-yl)oxy]cyclobutanecarboxylic acid

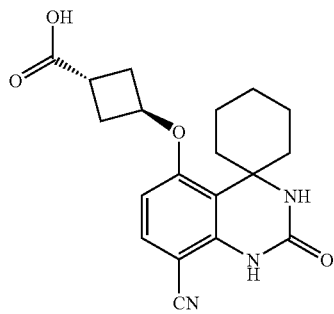

By the method of Example 1, starting with the compound of Preparation 16 (101 mg, 0.296 mmol) and using chromium (VI) oxide (0.5 mg, 0.005 mmol) and periodic acid (167 mg, 0.733 mmol) was obtained the title compound (76 mg, 72%).

$^1$H-NMR (400 MHz, D$_6$-DMSO) δ: 1.1-1.85 (m, 8H), 2.3-2.7 (m, 6H), 3.10 (m, 1H), 4.92 (m, (d, 1H), 7.14 (s, 1H), 7.51 (d, 1H), 8.51 (s, 1H).

LC-MS: retention time=2.49 minutes (100%), LRMS (ESI) m/z 356 [MH$^+$]

Example 5

1-[(8'-fluoro-2'-oxo-2',3'-dihydro-1'H-spiro[cyclohexane-1,4'-quinazolin]-5'-yl)oxymethyl]cyclobutanecarboxylic acid

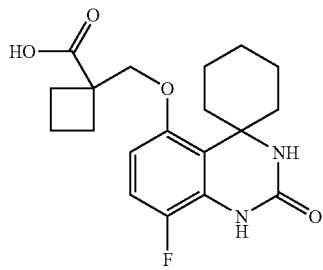

(a) 1-[(8'-fluoro-2'-oxo-2',3'-dihydro-1'H-spiro[cyclohexane-1,4'-quinazolin]-5'-yl)oxymethyl]cyclobutanecarboxylic acid methyl ester

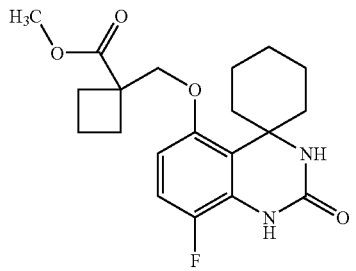

To a solution of 8'-fluoro-5'-hydroxy-1'H-spiro[cyclohexane-1,4'-quinazolin]-2'(3'H)-one (120 mg, 0.48 mmol) (described in WO 2004/026818) in DMF (1 ml) at room temperature was added cesium carbonate (234 mg, 0.72 mmol) and the mixture stirred for 10 minutes before addition of a solution of the compound of Preparation 18 (172 mg, 0.58 mmol) in DMF (1 ml). The reaction mixture was heated to 80° C. for 18 hours and then cooled to room temperature. The mixture was diluted with ethyl acetate (20 ml) and water (20 ml), the organic layer was separated and the aqueous layer extracted with ethyl acetate (20 ml). The combined organic layers were washed with water (2×20 ml) and brine (2×20 ml), dried over magnesium sulphate, filtered and evaporated in vacuo. The pale brown oil was triturated from diethyl ether (10 ml) to provide the title compound as a pale brown solid (140 mg of a solvate containing 0.3 mol DMF, 0.35 mmol, 73%).

$^1$H-NMR (400 MHz, D$_6$-DMSO): δ 1.16 (m, 1H), 1.35 (m, 2H), 1.49 (m, 3H), 1.72 (m, 2H), 1.90 (m, 1H), 2.03 (m, 3H), 2.26 (m, 2H), 2.42 (m, 2H), 3.60 (s, 3H), 4.22 (s, 2H), 6.52 (dd, 1H), 6.79 (s, 1H), 7.01 (t, 1H), 8.85 (s, 1H).

(b) 1-[(8'-fluoro-2'-oxo-2',3'-dihydro-1'H-spiro[cyclohexane-1,4'-quinazolin]-5'-yl)oxymethyl]cyclobutanecarboxylic acid To a partial solution of the product of step (a) (140 mg, 0.35 mmol) in methanol/water (1:1, 2ml) was added sodium hydroxide (28 mg, 0.70 mmol) and the reaction stirred at 50° C. for 24 hours. The mixture was cooled to room temperature and stirred for a further 6 days before treatment with a 2N aqueous solution of hydrochloric acid (2 ml). The resulting cream solid was collected by filtration, washed with water and dried in vacuo to provide the title compound (83 mg, 0.23 mmol, 65%).

$^1$H-NMR (400 MHz, D$_6$-DMSO): δ 1.25 (m, 1H), 1.37 (m, 2H), 1.49 (m, 3H), 1.71 (m, 2H), 1.90 (m, 1H), 2.01 (m, 3H), 2.38 (m, 4H), 4.18 (s, 2H), 6.52 (dd, 1H), 6.71 (s, 1H), 7.00 (dd, 1H), 8.78 (s, 1H), 12.43 (s, 1H).

LRMS m/z (ESI) 377 [M+H]$^+$

Example 6

Trans-3-[(8'-chloro-2'-oxo-2',3'-dihydro-1'H-spiro[cycloheptyl-1,4'-quinazolin]-5'-yl)oxy]cyclobutanecarboxylic acid

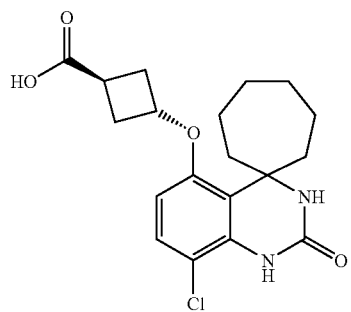

(a) Trans-3-[(8'-chloro-2'-oxo-2',3'-dihydro-1'H-spiro[cycloheptyl-1,4'-quinazolin]-5'-yl)oxy]cyclobutanecarboxylic acid ethyl ester

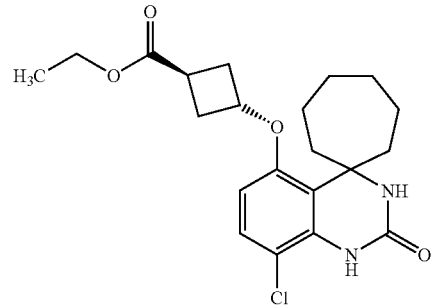

To a suspension of the compound of Preparation 20 (100 mg, 0.36 mmol), potassium carbonate (57 mg, 0.41 mmol) and 18-crown-6 (110 mg, 0.41 mmol) in dimethylformamide (3ml) at 80° C., was added a solution of 3-(toluene-4-sulphonyloxy)-cis-cyclobutanecarboxylic acid ethyl ester (prepared by a method analogous to the compound of Preparation 22) (123 mg, 0.41 mmol) in dimethylformamide (1 ml) and the reaction mixture stirred at 80° C. for 18 hours. The mixture was cooled to room temperature and extracted twice from water (30 ml) into ethyl acetate (2×20 ml). The combined organic layers were washed with brine (2×20 ml), dried over magnesium sulphate, filtered, and evaporated in vacuo. The oily residue was re-evaporated from methanol and triturated with diethyl ether to yield the title compound as a cream solid (75 mg, 0.18 mmol, 51%).

$^1$H-NMR (400 MHz, D$_6$-DMSO): δ 1.19 (t, 3H), 1.43-1.77 (m, 10H), 2.24 (m, 2H), 2.38 (m, 2H), 2.63 (m, 2H), 3.14 (m, 1H), 4.09 (q, 2H), 4.82 (m, 1H), 6.36 (d, 1H), 7.17 (d, 1H), 1H), 7.29 (s, 1H), 8.05 (s, 1H).

LRMS m/z (ESI) 407 [MH]$^+$ (b) Trans-3-[(8'-chloro-2'-oxo-2',3'-dihydro-1'H-spiro[cycloheptyl-1,4'-quinazolin]-5'-yl)oxy]cyclobutanecarboxylic acid To a suspension of the compound of step (a) (70 mg, 0.17 mmol) in methanol (1 ml) was added a solution of sodium hydroxide (14 mg, 0.35 mmol) in water (1 ml) and the resulting suspension stirred at 40° C. for 2 hours. The methanol was removed in vacuo and the pH of the resulting solution adjusted to ~1 by dropwise addition of 2N aqueous HCl (5 ml). The resulting solid was filtered and washed with isopropanol (1.5 ml) to yield the title compound as a white solid (25 mg, 0.066 mmol, 40%).

$^1$H-NMR (400 MHz, D$_6$-DMSO): δ 1.43-1.77 (m, 10H), 2.23 (m, 2H), 2.34 (m, 2H), 2.61 (m, 2H), 3.06 (m, 1H), 4.81 (q, 1H), 6.36 (d, 1H), 7.17 (d, 1H), 7.29 (s, 1H), 8.05 (s, 1H), 12.35 (s, 1H).

LRMS m/z (ESI) 755 [2M−H]$^-$

Example 7

Trans-3-[(8'-chloro-2'-oxo-2',3'-dihydro-1'H-spiro[cyclopentyl-1,4'-quinazolin]-5'-yl)oxy]cyclobutanecarboxylic acid

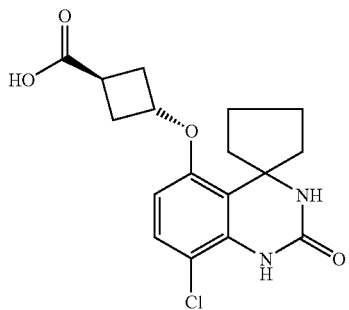

(a) Trans-3-[(8'-chloro-2'-oxo-2',3'-dihydro-1'H-spiro[cyclopentyl-1,4'-quinazolin]-5'-yl)oxy]cyclobutanecarboxylic acid tert-butyl ester

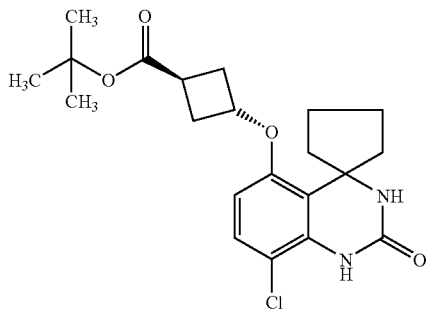

(a) To a partial solution of the compound of Preparation 24 (300 mg, 1.14 mmol) in DMF (3 ml) was added cesium carbonate (559 mg, 1.72 mmol) and the reaction mixture heated to 40° C. for 10 minutes before addition of a solution of the crude compound of Preparation 22 (523 mg, 1.60 mmol) in DMF (3mL) in one portion. The reaction mixture was heated to 80° C. for a further 9 hours and allowed to cool to room temperature. Water (3 ml) was then added to the reaction mixture followed by ethyl acetate (5ml) and collection of the resulting precipitate was attempted but was not successful. Complete dissolution quickly followed and the reaction mixture was concentrated to 2 ml in vacuo, water (5 mL) was added to induce crystallisation and the resulting product filtered off and dried in vacuo to give the title compound (310 mg, 0.76 mmol, 67%). LC-MS indicated 10% starting phenol remaining. This material was used in step (b) without further purification.

LRMS m/z (ESI) 407 [M+H]$^+$ (b) Trans-3-[(8'-chloro-2'-oxo-2',3'-dihydro-1'H-spiro[cyclopentyl-1,4'-quinazolin]-5'-yl)oxy]cyclobutanecarboxylic acid To a solution of the product of step (a) (310 mg, 0.76 mmol) in acetic acid (3 ml) at 60° C. was added 48% aqueous hydrobromic acid (0.5 ml) and the reaction stirred at room temperature for 30 minutes. The mixture was quenched by dropwise addition of water (0.1 ml) until slight turbidity was observed. The reaction was allowed to cool to room temperature before filtering the resulting precipitate to give a pale brown solid (130 mg). Purification was accomplished by re-crystallisation in acetic acid (1.5 ml)/water (0.1 ml) to provide the title compound as an off-white solid (35 mg, 0.09 mmol, 9%).

$^1$H-NMR (400 MHz, D$_6$-DMSO): δ 1.70 (m, 4H), 1.82 (m, 2H), 2.27 (m, 2H), 2.60 (m, 2H), 3.04 (m, 2H), 4.81 (m, 1H), 6.35 (d, 1H), 7.18 (d, 1H), 7.30 (s, 1H), 7.98 (s, 1H), 12.14 (s, 1H).

LRMS (ESI) m/z 351 [M+H]$^+$

PREPARATIONS

Preparation 1

3-[(Benzyloxy)methyl]-2,2-dichlorocyclobutanone

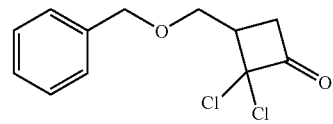

Zinc dust (6.54 g, 0.1 mol) was suspended in water (30 ml) and argon bubbled through the suspension for 15 minutes before the addition of copper (II) sulphate (780 mg, 3.1 mmol). The reaction mixture was stirred at room temperature, under argon for 30 minutes. The mixture was filtered under a stream of argon and the solid washed with water (100 ml), acetone (100 ml) and dried in vacuo for 4 hours. The resultant zinc/copper couple was suspended in diethyl ether:1,2-dimethoxyethane (70 ml:10 ml) under argon and allyl benzyl ether (4.6 ml, 30 mmol) added. A solution of trichloroacetyl chloride (9 ml, 81 mmol) in diethyl ether:1,2-dimethoxyethane (58 ml:7 ml) was added dropwise over 45 minutes and the reaction mixture heated to reflux for 48 hours. The reaction mixture was filtered through Celite® and the salts washed with diethyl ether (3×70 ml). The filtrate was evaporated in vacuo and the residue redissolved in hexane (150 ml). The remaining solids were removed by filtration and the filtrate washed with a saturated aqueous solution of sodium hydrogen carbonate (2×100 ml), brine (80 ml), dried over magnesium sulphate, filtered and evaporated in vacuo. The crude material was purified by column chromatography over silica gel eluting with 10-25% hexane:diethyl ether. The title compound was obtained as a yellow oil (7.03 g, 27.3 mmol, 91%).

$^1$H-NMR (CDCl$_3$, 400 MHz): δ 3.11-3.21 (m, 2H), 3.48 (m, 1H), 3.70 (m, 1H), 3.85 (m, 1H), 7.35 (m, 5H), 4.58 (s, 2H).

Preparation 2

3-[(Benzyloxy)methyl]cyclobutanone

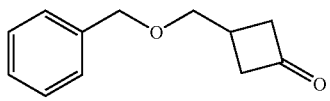

To a solution of the dichlorocyclobutanone of Preparation 1 (5.98 g, 23.08 mmol) in methanol saturated with ammonium chloride (90 ml) was added zinc powder (9.25 g, 142 mmol) and the reaction mixture stirred at room temperature for 2 hours. Ammonium chloride was added and the reaction mixture stirred at room temperature for a further 6 hours. The mixture was filtered through Celite® and the salts washed with diethyl ether (50 ml). The filtrate was concentrated in vacuo and the residue partitioned between diethyl ether (200 ml) and water (100 ml). The mixture was filtered and the organic phase washed with water, dried over magnesium sulphate, filtered and evaporated in vacuo. The title compound was obtained as a yellow oil (3.7 g, 19.5 mmol, 84%).

$^1$H-NMR (CDCl$_3$, 400 MHz): δ 2.69 (m, 1H), 2.90 (m, 2H), 3.11 (m, 2H), 3.60 (d, 2H), 4.56 (s, 2H), 7.34 (m, 5H).

Preparation 3

Cis-3-[(benzyloxy)methyl]cyclobutanol

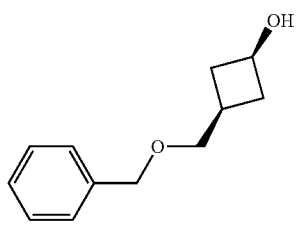

To a solution of the cyclobutanone of Preparation 2 (1.166 g, 6.13 mmol) in tetrahydrofuran stirring at −70° C., was added dropwise a 1M solution of lithium tri-sec-butylborohydride in tetrahydrofuran (40 ml), maintaining the reaction temperature below −65° C. The reaction was allowed to warm to room temperature over 18 hours. The reaction mixture was quenched with a saturated aqueous solution of sodium hydrogen carbonate (25 ml) then cooled to 5° C. 30% Aqueous hydrogen peroxide (4 ml) was added dropwise, maintaining the reaction temperature below 10° C. The mixture was extracted from water into ethyl acetate (50 ml) and the combined organic phases washed with brine (30 ml), dried over magnesium sulphate, filtered and evaporated in vacuo. The crude material was purified by column chromatography over silica gel eluting with 25-50% ethyl acetate:pentane to yield a colourless oil (1.05 g, 5.5 mmol, 89%). $^1$H-NMR indicated that a 15:1 ratio of cis:trans isomers had been obtained.

$^1$H-NMR (CDCl$_3$, 400 MHz): δ 1.70 (m, 2H), 2.10 (m, 1H), 2.46 (m, 2H), 3.45 (d, 2H), 4.15 (q, 1H), 4.52 (s, 2H), 7.33 (m, 5H).

Preparation 4

Trans-3-[(benzyloxy)methyl]cyclobutyl 4-nitrobenzoate

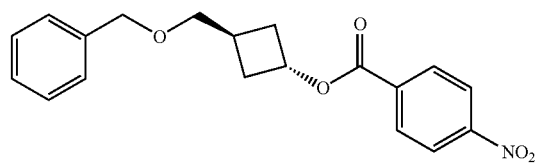

A solution of diethyl azodicarboxylate (2 g, 11.5 mmol) in tetrahydrofuran (5 ml) was added dropwise to a stirred solution of the cyclobutyl alcohol of Preparation 3 (1.05 g, 5.47 mmol), 4-nitrobenzoic acid (1.82 g, 10.9 mmol) and triphenylphosphine (3.016 g, 11.5 mmol) in tetrahydrofuran (20 ml) at 0° C. The reaction mixture was stirred at room temperature for 18 hours. The solvent was evaporated in vacuo and the residue redissolved in diethyl ether (30 ml). The remaining solid was removed by filtration and the filtrate evaporated in vacuo. The crude material was purified by column chromatography over silica gel eluting with 1:10 to 1:3 ethyl acetate:pentane to yield a colourless oil (1.64 g, 4.8 mmol, 88%). $^1$H-NMR indicated that a 15:1 ratio of trans:cis isomers had been obtained.

$^1$H-NMR (CDCl$_3$, 400 MHz): δ 2.40 (m, 4H), 2.67 (m, 1H), 3.53 (d, 2H), 4.57 (s, 2H), 5.36 (q, 1H), 7.37 (m, 5H), 8.20 (d, 2H), 8.29 (d, 2H).

Preparation 5

Trans-3-[(benzyloxy)methyl]cyclobutanol

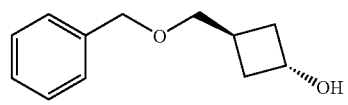

To a solution of the p-nitroester of Preparation 4 (1.64 g, 4.8 mmol) in 1,4-dioxane (35 ml) was added a solution of sodium hydroxide (385 mg, 9.6 mmol) in water (25 ml) and the reaction mixture stirred at room temperature for 30 minutes. Acetic acid (0.4 ml, 7 mmol) was added and the mixture concentrated in vacuo. The residue was extracted from a saturated aqueous solution of sodium hydrogen carbonate into ethyl acetate (20 ml), dried over magnesium sulphate, filtered and evaporated in vacuo. The title compound was obtained as a yellow oil (850 mg, 4.4 mmol, 92%).

¹H-NMR (CDCl₃, 400MHz): δ 2.08 (m, 2H), 2.20 (m, 2H), 2.47 (m, 1H), 3.47 (d, 2H), 4.39 (q,1H), 4.52 (s, 2H), 7.34 (m, 5H).

Preparation 6

Trans-3-[(benzyloxy)methyl]cyclobutyl p-toluenesulphonate

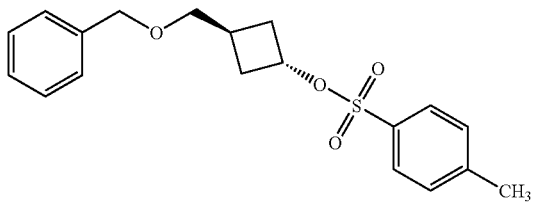

p-Toluenesulphonyl chloride (1.18 g, 6.2 mmol) was added portionwise to a stirred solution of the cyclobutanol of Preparation 5 (850 mg, 4.42 mmol) in pyridine (5 ml) at 0° C. and the reaction mixture stirred at room temperature for 18 hours. The solvent was concentrated in vacuo and the residue redissolved in ethyl acetate (30 ml), washed with 2N hydrochloric acid, (30 ml) a saturated aqueous solution of sodium hydrogen carbonate (30 ml), brine (30ml), dried over magnesium sulphate, filtered and evaporated in vacuo. The crude material was purified by column chromatography over silica gel eluting with dichloromethane. The title compound was obtained as a colourless oil (1.53 g, 4.4 mmol).

¹H-NMR (CDCl₃, 400 MHz): δ 2.15 (m, 2H), 2.31 (m, 2H), 2.44 (s, 3H), 2.49 (m, 1H), 3.4 (d, 2H), 4.49 (s, 2H), 4.93 (q, 1H), 7.32 (m, 7H), 7.75 (d, 2H).

Preparation 7

5'-({Cis-3-[(benzyloxy)methyl]cyclobutyl}oxy)-8'-chloro-1'H-spiro[cyclohexane-1,4'-quinazolin]-2'(3'H)-one

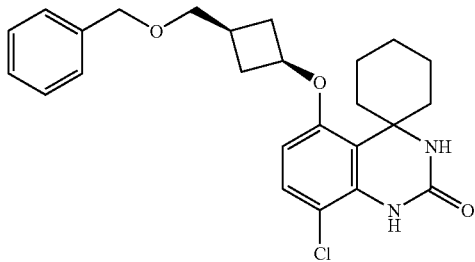

8'-Chloro-5'-hydroxy-1'H-spiro[cyclohexane-1,4'-quinazolin]-2'(3'H)-one (prepared as described in *Bioorg. Med. Chem. Lett*, (2004), 14 (18), 4627-4632) (640 mg, 2.4 mmol), potassium carbonate (400 mg, 2.9 mmol) and 18-crown-6 (767 mg, 2.9 mmol) were combined in dimethylformamide (8 ml) and the reaction mixture heated to 80° C. A solution of the tosylate of Preparation 6 (1 g, 2.9 mmol) in dimethylformamide was added in 3 portions and the mixture heated at 80° C. for a further 18 hours. The reaction mixture was partitioned between ethyl acetate (100 ml) and water (150 ml) and the solid collected by filtration. The phases were separated and the aqueous phase reextracted with ethyl acetate, diluted with brine and again extracted into ethyl acetate. The combined organic phases were concentrated in vacuo and the residue triturated with water and methanol. The combined crude products were purified by column chromatography over silica gel eluting with dichloromethane to dichloromethane:ethyl acetate (1:1) to obtain the title compound as an off-white solid (685 mg, 1.156 mmol, 64%).

¹H-NMR (D₆-DMSO, 400MHz): δ 1.1 (m, 1H), 1.4 (m, 2H), 1.6 (m, 3H), 1.7 (m, 2H), 1.8 (m, 2H), 2.3 (m, 1H), 2.5 (m, 4H), 3.4 (s, 2H), 4.4 (s, 2H), 4.6 (m, 1H), 6.4 (d, 1H), 7.0 (s, 1H), 7.2 (d, 1H), 7.3 (m, 5H), 7.8 (s, 1H).

Preparation 8

8'-Chloro-5'-{[cis-3-(hydroxymethyl)cyclobutyl]oxy}-1'H-spiro[cyclohexane-1,4'-quinazolin]-2'(3'H)-one

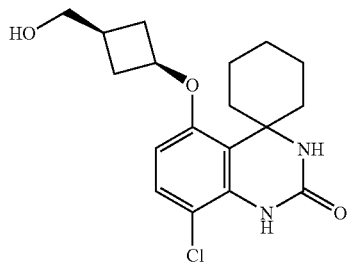

A 2M solution of boron trichloride-dimethyl sulfide complex in dichloromethane (1.8 ml, 3.6 mmol) was added to a suspension of the benzyl alcohol of Preparation 7 (400 mg, 0.9 mmol) in dichloromethane (10 ml) and the reaction mixture stirred at room temperature overnight. A saturated aqueous solution of sodium hydrogen carbonate (10 ml) was added and the mixture stirred for 5 minutes. Dichloromethane and water were added and the resultant solid collected by filtration. The title compound was obtained as a white solid (230 mg, 0.657 mmol, 73%).

¹H-NMR (D₆-DMSO, 400 MHz): δ 1.17 (m, 1H), 1.42 (m, 2H), 1.57 (m, 3H), 1.82 (m, 4H) 2.05 (m, 1H), 2.45 (m, 4H), 3.38 (t, 2H), 4.58 (m, 2H), 6.41 (d, 1H), 6.99 (s, 1H), 7.20 (d, 1H), 7.86 (s, 1H). LRMS m/z (APCI) 351 [MH]⁺

Preparation 9

Cis-3-[(benzyloxy)methyl]cyclobutyl p-toluenesulphonate

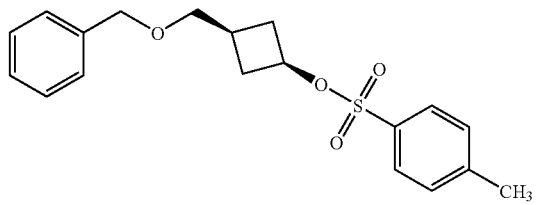

Pyridine (14.3 ml, 176 mmol) and p-toluenesulphonyl chloride (20.2 g, 105.9 mmol) were added to a solution of the alcohol of Preparation 3 (17 g, 88.4 mmol) in dichloromethane (90 ml) stirring at 5° C. and the reaction mixture was stirred at room temperature for 18 hours. The reaction mixture was diluted with dichloromethane (50 ml), washed with 2N hydrochloric acid (50 ml), a saturated aqueous solution of sodium hydrogen carbonate (50 ml), dried over magnesium sulphate, filtered and evaporated in vacuo. The crude material was purified by column chromatography over silica gel eluting with pentane:ethyl acetate (19:1, 9:1, 4:1). The title compound was obtained as a colourless oil (24.8 g, 71.6 mmol, 81%).

$^1$H-NMR (CDCl$_3$, 400 MHz): δ 1.95 (m, 2H), 2.1 (m, 1H), 2.35 (m, 2H), 2.45 (s, 3H), 3.4 (m, 2H), 4.5 (s, 2H), 4.7 (m, 1H), 7.3 (m, 7H), 7.8 (m, 2H).

LRMS m/z (ESI) 347 [MH]$^+$

Preparation 10

5'-({Trans-3-[(benzyloxy)methyl]cyclobutyl}oxy)-8'-chloro-1'H-spiro[cyclohexane-1,4'-quinazolin]-2'(3'H)-one

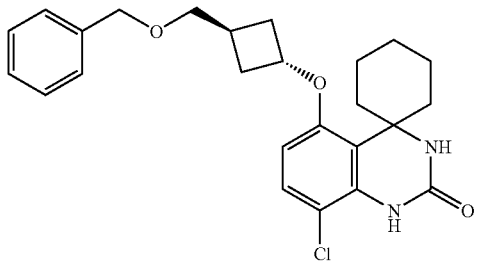

Method A

Caesium carbonate (730 mg, 2.24 mmol) was added to a stirred suspension of 8'-chloro-5'-hydroxy-1'H-spiro[cyclohexane-1,4'-quinazolin]-2'(3'H)-one (500 mg, 1.87 mmol) in dimethylformamide (2 ml) and the reaction mixture heated to 80° C. After 5 minutes a solution of the tosylate of Preparation 9 (710 mg, 2.05 mmol) in dimethylformamide (1 ml) was added and the reaction mixture heated at 80° C. for 18 hours. The mixture was extracted from brine (60 ml) into ethyl acetate (1×80 ml, 2×30 ml), washed with brine (3×100 ml), dried over magnesium sulphate, filtered and evaporated in vacuo. The title compound was obtained as a slightly impure cream solid (800 mg, 0.96 mmol, 96%).

Method B

To a solution of 8'-chloro-5'-hydroxy-1'H-spiro[cyclohexane-1,4'-quinazolin]-2'(3'H)-one (950 mg, 3.56 mmol) in dimethylformamide (12 ml) stirring at 80° C. was added potassium carbonate (590 mg, 4.27 mmol) and 18-crown-6 (1.1 g, 4.27 mmol). The reaction mixture was stirred for 10 minutes before the addition of a solution of the tosylate of Preparation 9 (1.48 g, 4.27 mmol) in dimethylformamide (3 ml). The reaction mixture was heated at 80° C. for 24 hours. The mixture was poured onto water: methanol (75 ml:25 ml), stirred for 10 minutes and the resulting precipitate collected by filtration and washed with methanol. The solid was dissolved in dichloromethane, filtered through Celite® and the resulting filtrate evaporated in vacuo to yield the title compound as a 9:1 mixture of trans:cis isomers (887 mg, 2.0 mmol, 56%).

$^1$H-NMR (CDCl$_3$, 400 MHz): δ 1.3 (m, 1H), 1.5-1.9 (m, 9H), 2.4 (m, 3H), 2.6 (m, 2H), 3.5 (d, 2H), 4.6 (s, 2H), 4.75 (m, 1H), 5.85 (bs, 1H), 6.25 (d, 1H), 7.05 (bs, 1H), 7.1 (d, 1H), 7.3-7.4 (m, 5H).

LRMS m/z (ESI) 441 [MH]$^+$

Preparation 11

8'-Chloro-5'-{[trans-3-(hydroxymethyl)cyclobutyl]oxy}-1'H-spiro[cyclohexane-1,4'-quinazolin]-2'(3'H)-one

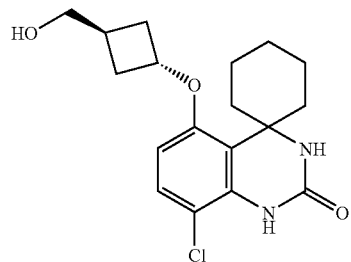

A 2M solution of boron trichloride-dimethyl sulfide complex in dichloromethane (15 ml) was added dropwise to a solution of the benzyl ether of Preparation 10 (3.5 g, 7.9 mmol) in dichloromethane (80 ml) and the reaction mixture stirred at room temperature for 18 hours. The mixture was poured into a saturated aqueous solution of sodium hydrogen carbonate (200 ml) and stirred until the effervescence ceased. The mixture was extracted into dichloromethane (1×200 ml, 2×100 ml), washed with brine (50 ml), dried over magnesium sulphate, filtered and evaporated in vacuo. The crude material was recrystallised from acetonitrile to yield the title compound as a 91:9 ratio of trans:cis products (2.33 g, 6.65 mmol, 84%).

$^1$H-NMR (CDCl$_3$, 400 MHz): δ 1.3 (m, 1H), 1.5 (m, 2H), 1.8 (m, 5H), 2.4 (m, 4H), 2.6 (m, 3H), 3.8 (d, 2H), 4.8 (m, 1H), 5.7 (bs, 1H), 6.25 (d, 1H), 7.0 (bs, 1H), 7.1 (d, 1H).

LRMS m/z (ESI) 351 [MH]$^+$

Preparation 12

3-methylenecyclobutanecarboxylic acid

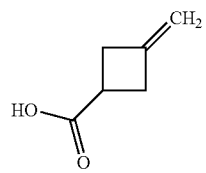

Potassium hydroxide (17.37 g, 214.7 mmol) was dissolved in water (20 ml) and ethanol (20 ml) added. When cool this solution was added to 3-methylene-cyclobutanecarbonitrile (5.0 g, 53.7 mmol) and the resulting solution heated to reflux for 2.5 hours, allowed to cool and evaporated in vacuo to a cream solid. The solid was dissolved in water (15 ml) and cooled in an ice bath, concentrated HCl added to pH 1 and extracted with diethyl ether (3×20 ml). The ethereal extracts were dried over magnesium sulphate and evaporated in vacuo to yield the title compound as a pale yellow liquid (5.6 g, 93%).

$^1$H-NMR (CDCl$_3$, 400 MHz): δ 2.95 (m, 2H), 3.02 (m, 2H), 3.17 (m, 1H), 4.82 (m, 2H) (1 exchangeable proton not seen).

Preparation 13

3-methylenecyclobutanecarboxylic acid benzyl ester

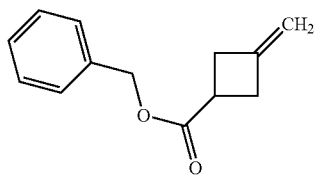

A suspension of 1,1'-carbonyldiimidazole (1.59 g, 9.81 mmol) in ethyl acetate (5 ml) was added in portions to a solution of the product of Preparation 12 (1 g, 8.9 mmol) in ethyl acetate (5 ml). Gentle effervescence was observed. The mixture was stirred at room temperature for about 1.5 hours, benzyl alcohol (1.11 ml, 10.7 mmol) added and stirring continued overnight. The solution was diluted with diethyl ether (20 ml), washed with water (2×10 ml), dried over magnesium sulphate and evaporated in vacuo to a colourless liquid which was purified by filtering through 10 g SiO$_2$, eluting with dichloromethane, to give the title compound as a colourless oil (1.246 g, 69%).

$^1$H-NMR (CDCl$_3$, 400 MHz): δ 2.92 (m, 2H), 3.02 (m, 2H), 3.16 (m, 2H), 4.80 (m, 2H), 5.15 (s, 2H), 7.36 (m, 5H).

LRMS m/z (ESI) 203 [MH]$^+$

Preparation 14

3-(hydroxymethyl)cyclobutane carboxylic acid benzyl ester

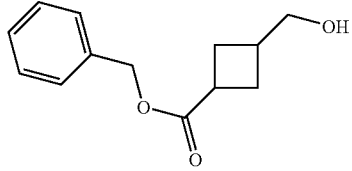

Borane-dimethyl sulphide (0.07 ml, 0.72 mmol) was diluted with THF (1 ml) and added dropwise at room temperature to a stirred solution of the compound of Preparation 13 (300 mg, 1.48 mmol) in THF (1 ml). The colourless solution was stirred at room temperature for 1 hour and then a solution of sodium perborate (145 mg, 1.78 mmol) in water (1 ml) added dropwise at a rate that controlled the effervescence. Once addition was complete, the mixture was diluted with 1,4-dioxane (1 ml) and the resulting solution warmed at 60° C. for 1 hour, quenched by addition of water (5 ml) and extracted with ethyl acetate (10 ml). The ethyl acetate extract was dried over magnesium sulphate and evaporated in vacuo to yield a colourless oil (226 mg, 69%) which was used as such in the next step.

$^1$H-NMR (CDCl$_3$, 400 MHz): δ 2.05 (m, 2H), 2.33 (m, 2H), 2.45 (m, 1H), 3.11 (m, 1H), 3.62 (dd, 2H), 5.13 (d, 2H), 7.35 (m, 5H).

Preparation 15

3-(p-toluenesulphonyloxymethyl)cyclobutane-1-carboxylic acid benzyl ester

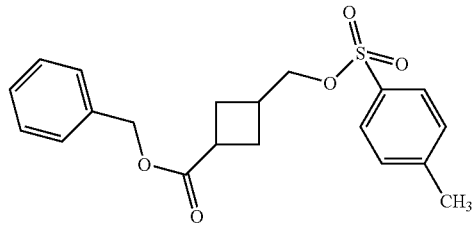

A solution of p-toluenesulphonyl chloride (309 mg, 1.62 mmol) in dichloromethane (2 ml) was added dropwise to a stirred solution of the compound of Preparation 14 (275 mg, 1.25 mmol) and pyridine (0.26 ml, 3.25 mmol) at room temperature, and stirring continued for 3 days. The mixture was partitioned between dichloromethane (20 ml) and water (2×20 ml), the dichloromethane extract dried over magnesium sulphate and evaporated in vacuo to a colourless oil which was purified by column chromatography over silica gel eluting with dichloromethane to 1:1 diethyl ether:dichloromethane to obtain the title compound (226 mg, 48%) as a colourless oil.

$^1$H-NMR (CDCl$_3$, 400 MHz): δ 2.02 (m, 2H), 2.25-2.41 (m, 2H), 2.44 (s, 3H), 2.55-2.75 (m, 1H), 3.07(m, 1H), 4.00 (2×d, 2H), 5.10 (d, 2H), 7.34 (m, 7H), 7.78 (m, 2H).

Preparation 16

5'-{[trans-3-(hydroxymethyl)cyclobutyl]oxy}-2'-oxo-2',3'-dihydro-1'H-spiro[cyclohexane-1,4'-quinazoline]-8'-carbonitrile

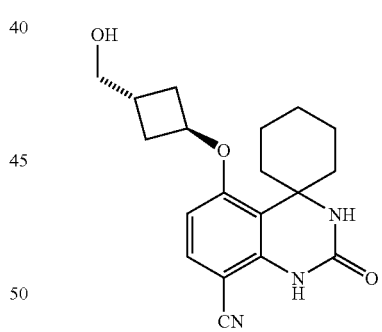

Sodium cyanide (27.9 mg, 0.57 mmol) followed by nickel bromide (62.3 mg, 0.285 mmol) were added to a suspension of the compound of Preparation 11 (100 mg, 0.285 mmol) in N-methylpyrrolidinone (1.5 mL) and the reaction mixture heated in a microwave reactor for 10 minutes at 200° C. The mixture was partitioned between diethyl ether (2×20 ml) and water (10 mL), the combined organic extracts dried over magnesium sulphate and concentrated in vacuo to give the title compound as a pale orange/red solid (27.8 mg).

$^1$H-NMR (400 MHz, CDCl$_3$): δ 1.4-1.85 (m, 9H), 2.3-2.7 (m, 6H), 3.73 (d, 2H), 4.83 (m, 1H), 5.60 (s, 1H), 6.33 (d, 1H), 6.98 (s, 1H), 7.36 (d, 1H).

LC-MS: Retention time=2.54 minutes (100%), LRMS m/z 342 [MH$^+$]

Preparation 17

1-(hydroxymethyl)-cyclobutanecarboxylic acid methyl ester

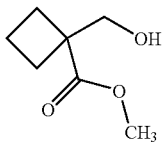

To a solution of 1,1-cyclobutanedicarboxylic acid dimethyl ester (available from Lancaster Synthesis Ltd, UK) (2.0 g, 11.6 mmol) in tetrahydrofuran (20 ml) at room temperature was added lithium tri-tert-butoxyaluminium hydride (25.5 ml of a 1M solution in tetrahydrofuran, 25.5 mmol) dropwise over 10 minutes. The reaction mixture was heated to gentle reflux for 3 hours, cooled to room temperature and stirred for 18 hours. The resulting suspension was diluted with saturated aqueous ammonium chloride (30 ml) and stirred vigorously for 15 minutes before filtering. The solid was washed with diethyl ether (50 ml), the organic layer separated and the aqueous layer extracted with diethyl ether (50 ml). The combined organic extracts were dried over magnesium sulphate, filtered and evaporated in vacuo to give the title compound as a colourless oil (1.8 g).

Preparation 18

1-(p-toluenesulphonyloxymethyl)-cyclobutanecarboxylic acid methyl ester

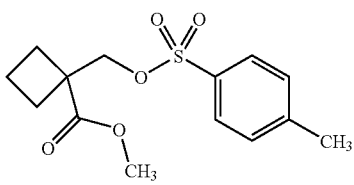

To a solution of the crude compound of Preparation 17 (1.6 g, 11.0 mmol) in dichloromethane (5 ml) was added p-toluenesulphonyl chloride (4.2 g, 22.0 mmol) followed by pyridine (2.7 ml, 33.0 mmol) and the solution stirred at room temperature for 18 hours. The reaction mixture was then diluted with dichloromethane (30 ml) and washed with 2N aqueous HCl (2×25 ml), saturated aqueous sodium bicarbonate (50 ml), dried over magnesium sulphate and evaporated in vacuo. The crude orange oil (5 g) was purified by flash chromatography on silica gel eluting with ethyl acetate:pentane (1:5) to yield the title compound as a colourless oil (1.7 g, 5.7 mmol, 49%).

$^1$H-NMR (CDCl$_3$, 400 MHz): δ 1.96 (m, 4H), 2.40 (m, 2H), 2.45 (s, 3H), 3.62 (s, 3H) 4.24 (s, 2H), 7.35 (d, 2H), 7.79 (d, 2H).

Preparation 19

8'Chloro-5'-methoxy-1'H-spiro[cycloheptyl-1,4'-quinazoline]-2'(3'H)-one

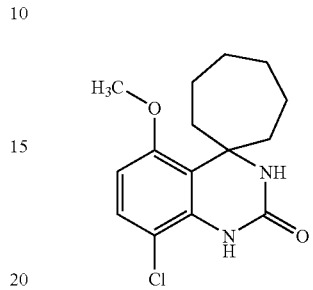

A solution of 2-chloro-5-methoxyphenylurea (WO 02/074754, intermediate 5) (17.9 g, 89.5 mmol) in cycloheptanone (60 ml, 0.51 mol) was added dropwise to polyphosphoric acid (213 g) at 100° C. over 20 minutes (an exotherm to 127° C. was noted) and heated for 1 hour. The mixture was poured into water (3 liters) and ethyl acetate (1 liter) with stirring. The resulting solid was collected by filtration, washed well with ethyl acetate and dried. The dried solid was dissolved in chloroform, washed with aqueous sodium bicarbonate, dried over sodium sulphate and concentrated in vacuo to give the title compound as a white solid (10.2 g, 34 mmol, 39%).

The biphasic filtrate was separated and the ethyl acetate phase washed with water and brine, dried over sodium sulphate and concentrated. The residue was triturated with t-butyl methyl ether and the resulting white solid collected by filtration, washed with further t-butyl methyl ether and dried to give a second portion of the title compound (9.0 g, 30.6 mmol, 34%).

$^1$H-NMR (400 MHz, CDCl$_3$): δ 1.53-1.84 (complex, 10H), 2.46 (m, 2H), 3.81 (s, 3H), 5.33 (br, 1H), 6.46 (d, 1H), 7.03 (br, 1H), 7.18 (d, 1H).

LRMS m/z 295 [M+H]$^+$

Preparation 20

8'-chloro-5'-hydroxy-1'H-spiro[cycloheptane-1,4'-quinazolin]-2'(3'H)-one

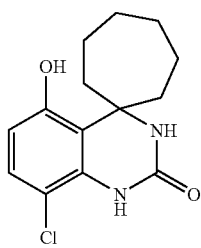

To a solution, in dichloromethane (500 ml), of the compound of Preparation 19 (19.0 g, 64.6 mmol) was added a 1M solution of boron tribromide in dichloromethane (129 ml, 129 mmol) and the mixture was stirred at room temperature for 3 days. The reaction mixture was poured into water (1.5 liters) and ethyl acetate (1 liter). The white solid was collected by filtration, the phases separated and the organic phase dried over sodium sulphate and concentrated in vacuo to give a brown solid. The filtered white solid was recrystallised from ethanol to give the title compound (7.4 g, 26.4 mmol, 41%). The mother liquors from the recrystallisation were combined with the brown solid and the mixture stirred in ethanol, filtered and dried to give a second batch of product (7.0 g, 25 mmol, 39%).

$^1$H-NMR (400 MHz, D$_6$-DMSO): δ 1.38-1.78 (complex, 10H), 2.26 (m, 2H), 6.40 (d, 1H), 7.02 (d,1H), 7.20 (br, 1H), 7.80 (br, 1H), 9.84 (br, 1H).

Preparation 21

Cis-3-hydroxycyclobutylcarboxylic acid tert-butyl ester

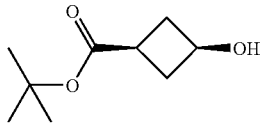

Method A

Tert-butyl 3-oxocyclobutanecarboxylic acid (*J. Org. Chem.* (1993) 58, 110), (3.10 g, 18.2 mmol) was dissolved in tetrahydrofuran:methanol (20:1, 30 ml) and cooled to 5° C. under nitrogen. Sodium borohydride (345 mg) was added in portions and the resulting clear solution stirred at 5° C. for 15 minutes before being diluted by the dropwise addition of water (135 ml) then ethyl acetate (135 ml). The aqueous phase was separated and washed with ethyl acetate (2×25 ml). The combined organic phases were washed with brine (20 ml), dried over magnesium sulphate and concentrated in vacuo to give the title compound as a slightly yellow oil (3.05 g, 17.7 mmol, 97%).

$^1$H-NMR (CDCl$_3$, 400 MHz): δ 1.46 (s, 9H), 2.12 (m, 2H), 2.55 (m, 3H), 4.17 (m, 1H).

GC analysis (sample in acetonitrile): retention time 4.57 minutes (91.5% area).

Method B 3-oxocyclobutanecarboxylic acid (*J. Org. Chem.* (1993) 58, 110), (10.0 g, 88 mmol) was dissolved in dichloromethane (20 ml) and cooled to 5° C. 4-Dimethylaminopyridine (8.6 g, 70 mmol) was added portionwise followed by tert-butanol (13.0 g, 176 mmol) in one portion. A 1M solution of N,N'-dicyclohexylcarbodiimide in dichloromethane (96 ml, 96 mmol) was added dropwise keeping the temperature between 0° and 5° C. The resulting slurry was warmed to room temperature and stirred overnight. Following filtration, the filtrate was added dropwise to 2M hydrochloric acid (50 ml) at 5° C. The resulting phases were separated and the lower organic layer was allowed to warm to room temperature and washed with water (50 ml) and saturated sodium bicarbonate solution (50 ml). The lower organic phase was concentrated by distillation and was solvent exchanged with tetrahydrofuran. The final reaction volume was 30 ml. Methanol (6 ml) was added. Meanwhile sodium borohydride (1.65 g, 44 mmol) was suspended in tetrahydrofuran (39 ml) and cooled to 5° C. The intermediate tetrahydrofuran solution was added dropwise to the slurry of sodium borohydride keeping the temperature between 0° and 5° C. The reaction was then stirred for 2 hours at 0-5° C. Water was added dropwise keeping the temperature between 0° C. and 5° C. Ethyl acetate (75 ml) was added and the phases separated. The lower aqueous layer was allowed warm to room temperature and was washed with ethyl acetate (37 ml). The combined organic layers were concentrated and further washed with brine (37 ml) followed by water (37 ml). The upper organic layer was stripped under vacuum to give the title compound as a yellow oil (10.1 g, 58.6 mmol, 67%).

$^1$H-NMR (CDCl$_3$, 400 MHz): δ 1.46 (s, 9H), 2.12 (m, 2H), 2.55 (m, 3H), 4.17 (m, 1H). GC analysis: retention time 9.02 minutes (cis isomer) (87.5% area), retention time 9.07 minutes (trans isomer) (10.0% area).

Preparation 22

3-(p-toluenesulphonyloxy)-cyclobutanecarboxylic acid tert-butyl ester

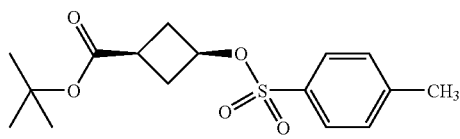

Method A

The compound of Preparation 21 (3.02 g, 17.35 mmol) was dissolved in pyridine (15 ml) and cooled to 0° C. under nitrogen. p-Toluenesulphonyl chloride (3.5 g, 18.4 mmol) was added in one portion and the solution stirred at room temperature for 72 hours. The resulting pink solution containing white suspended material was concentrated in vacuo, partitioned between 2N aqueous HCl (30 ml) and ethyl acetate (30 ml), and the aqueous layer washed again with ethyl acetate (15 ml). The combined organic layers were washed with 2N aqueous HCl (15 ml), saturated aqueous sodium bicarbonate (15 ml) and brine (30 ml), dried over concentrated in vacuo to give the title compound as an orange oil (5.15 g, 15.7 mmol, 90%) which solidified on standing.

$^1$H-NMR (400 MHz, CDCl$_3$): δ 1.43 (s, 9H), 2.32-2.57 (complex, 5H), 2.46 (s, 3H), 4.73 (m, 1H), 7.35 (d, 2H), 7.79 (d, 2H).

LC-MS: cis isomer retention time 21.78 minutes (81%), LRMS (ESI) m/z 327 [MH$^+$], trans isomer retention time 22.08 minutes (7.3%), LRMS (ESI) m/z 327 [MH$^+$].

Method B

The compound of Preparation 21 (10.0, 58 mmol) was dissolved in pyridine (25 ml) and cooled to 0° C. under nitrogen. p-Toluenesulphonyl chloride (16.6 g, 87 mmol) was dissolved in pyridine (25 ml) and added dropwise keeping the temperature between 0° and 5° C. The reaction was then allowed to warm to room temperature and stirred overnight.

The reaction was concentrated to a solid and slurried in ethyl acetate (50 ml). The slurry was cooled to 0-5° C., washed with 2M hydrochloric acid (75 ml) and the phases separated. The lower aqueous phase was back extracted with ethyl acetate (50 ml). The combined organic phases were washed with water (50 ml) and sodium hydrogen carbonate solution (50 ml). The organic phase was concentrated and cooled to 0°-5° C. N,N-Dimethylethylenediamine (3.5 g, 40 mmol) was added dropwise. The reaction mixture was washed with 2M hydrochloric acid (75 ml). The upper organic phase was washed with water (75 ml) and brine (75 ml). The organic phase was concentrated to a pale yellow oil which crystallised on standing (15.5 g, 47 mmol, 82%).

¹H-NMR (400 MHz, CDCl₃): δ 1.43 (s, 9H), 2.32-2.57 (complex, 5H), 2.46 (s, 3H), 4.73 (m, 1H), 7.35 (d, 2H), 7.79 (d, 2H).

GC analysis: retention time 15.98 minutes (cis isomer) (94.1% area), retention time 15.82 minutes (trans isomer) (5.9% area).

Preparation 23

8'Chloro-5'-methoxy-1'H-spiro[cyclopentyl-1,4'-quinazoline]-2'(3'H)-one

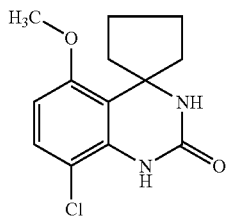

To 2-chloro-5-methoxyphenylurea (WO 02/074754, intermediate 5) (22.04 g, 0.11 mol) was added Eaton's reagent (a 7.7 wt. % solution of phosphorus (V) oxide in methanesulphonic acid) (440.8 ml) followed by cyclopentanone (19.5 ml, 0.22mol) and the resulting solution heated at 85° C. for 4 hours. The reaction was cooled to ~5° C. and water added cautiously keeping the temperature between 20 and 30° C. Dichloromethane (400 ml in total) and brine (200 ml) were then added and the phases separated. The aqueous phase was washed with dichloromethane (2×100 ml), the organic extracts combined and evaporated in vacuo to give a dark oil which was purified on a silica chromatography column eluting with dichloromethane:methanol (95:5 to 90:10) to give the product as a dark brown solid. The solid was triturated with diethyl ether and pentane, collected by filtration and dried to give the title compound as a brown solid (27.17 g, 0.1 mol, 92%).

¹H-NMR (400 MHz, CDCl₃): δ 1.7-1.8 (m, 6H), 2.4-2.5 (m, 2H), 3.7 (s, 3H), 5.75 (br s, 1H), 6.4 (d, 1H), 7.05 (s, 1H), 7.15 (d, 1H).

LRMS m/z (APCI) 267 [M+H]⁺

Preparation 24

8'-chloro-5'-hydroxy-1'H-spiro[cyclopentane-1,4'-quinazolin]-2'(3'H)-one

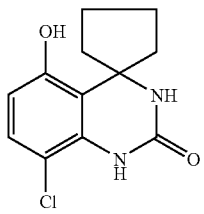

To the compound of Preparation 23 (25 g, 0.093 mol), was added acetic acid (250 ml) followed by 48% aqueous hydrobromic acid (207 ml, 1.86 mol) in one portion and the resulting solution stirred at 115° C. for 7 days. The reaction mixture was cooled to 100° C. and water (207 ml) was added dropwise. The mixture was concentrated in vacuo to precipitate a brown solid which was collected by filtration and washed with water (2×100 ml). A second portion of product was obtained from the filtrate on standing. The combined portions of product were dried by slurry with toluene (150 ml) and solvent removal in vacuo three times to give a grey solid which was pre-absorbed onto silica and purified by column chromatography eluting with dichloromethane:methanol (98:2 to 95:5 to 80:20). The product fractions were concentrated in vacuo and the resulting solid triturated with pentane and filtered to afford the title compound as a brown solid (10 g, 0.0395 mol, 42%).

¹H-NMR (400 MHz, D₆-DMSO) δ 1.6-1.8 (m, 6H), 2.3-2.4 (m, 2H), 6.4 (d, 1H), 7.11 (d, 1H), 7.2 (s, 1H), 7.8 (s, 1H), 9.9 (s, 1H).

LRMS m/z (ESI) 253 [M+H]⁺

Preparation 25

(2-Chloro-5-methoxyphenyl)urea

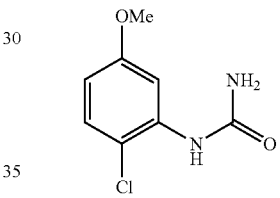

2-Chloro-5-methoxyaniline hydrochloride (26 g, 134 mmol) was added to acetic acid (117 ml) and water (13 ml). The slurry was warmed to 30° C. A solution of potassium cyanate (13 g, 161 mmol) in water (104 ml) was added dropwise. After 1 hour at 40° C., the reaction was cooled to 20° C., filtered and washed with water (78 ml). The product was dried overnight in vacuo at 60° C. to yield the title compound as a white solid (21.8 g, 81%).

¹H-NMR (300 MHz, D₆-DMSO): δ 3.71 (s, 3H), 6.41 (s, 2H), 6.53 (d, 1H), 7.26 (d, 1H), 7.85 (s, 1H), 7.98 (s, 1H).

LC-MS (ESI): 10.9 minutes 99.4 (%), m/z 201 [MH⁺]

Preparation 26

8'-Chloro-5'-methoxyspiro[cyclohexane-1,4'-quinazolin]-2'(1'H)-one

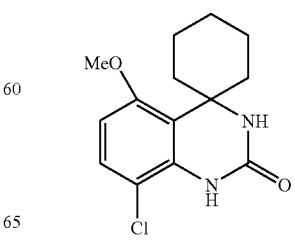

The compound of Preparation 25 (5.0 g, 25 mmol) was added to Eaton's Reagent (7% w/w solution of $P_2O_5$ in methanesulphonic acid) (150 g) to form a solution which was then heated to 60° C. Cyclohexanone (4.9 g, 50 mmol) was added over 10 minutes and the reaction then warmed to 80° C. and held at that temperature for 1 hour. The reaction mixture was then cooled to 5° C. and water was added (150 ml). The reaction mixture was then extracted with dichloromethane (100 ml) and the upper aqueous phase washed with dichloromethane (2×10 ml). The combined organic phases were concentrated before adding 2-propanol (110 ml). The reaction mixture was further concentrated at atmospheric pressure to remove the residual dichloromethane. The reaction was cooled to crystallise the product which was stirred at 5° C. for one hour. The product was collected by filtration and washed with 2-propanol (15 ml) before being dried for 18 hours at 50° C. to yield the title compound as a white solid (5.2 g, 19 mmol, 76%).

$^1$H-NMR (300 MHz, $D_6$-DMSO): δ 1.2 (m, 1H), 1.4 (m, 2H), 1.5 (m, 1H), 1.6 (m, 2H), 1.7 (m, 1H), 1.8 (m, 1H), 2.4 (t, 2H), 3.79 (s, 3H), 6.64 (d, 1H), 6.97 (s, 1H), 7.26 (d, 1H), 7.91 (s, 1H).

LC-MS (ESI): 18.5 minutes 97.4 (%), m/z 281 [MH$^+$]

Preparation 27

8'-Chloro-5'-hydroxyspiro[cyclohexane-1,4'-quinazolin]-2'(1'H)-one

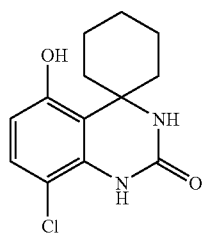

Step (a)

8'-Chloro-5'-hydroxyspiro[cyclohexane-1,4'-quinazolin]-2'(1'H)-one acetic acid solvate The compound of Preparation 26 (350 g, 1.24 mol) was slurried in acetic acid (3500 ml). Hydrobromic acid (48% w/w in water) (2800 ml, 24.8 mol) was added to the slurry at room temperature. The slurry was then warmed to reflux and stirred for 4 days. The reaction was cooled to 100° C. and water (2800 ml) added dropwise over 1 hour. The slurry was cooled to 10° C., stirred for one hour before being filtered, washed with water (1100 ml) and dried in the vacuum oven over night to yield the title compound as a white solid (344 g, 1.28 mol, 103%).

$^1$H-NMR ($D_6$-DMSO, 300 MHz): δ 1.2 (m, 1H), 1.4 (m, 2H), 1.5 (m, 1H), 1.6 (m, 2H), 1.7 (m, 1H), 1.8 (m, 1H), 1.9 (s, 3H, $CH_3COOH$), 2.4 (t, 2H), 6.45 (d, 1H), 6.95 (s, 1H), 7.1 (d, 1H), 7.75 (s, 1H), 9.9 (s, 1H, $CH_3COOH$).

LC-MS (ESI): 14.2, minutes 99.1 (%), m/z 267 [MH$^+$].

Step (b)

8'-Chloro-5'-hydroxyspiro[cyclohexane-1,4'-quinazolin]-2'(1'H)-one

The acetic acid solvate of step (a) (330 g, 1.24 mol) was slurried in acetone (730 ml) at room temperature for 6 hours. The product was then collected by filtration, washed with acetone (330 ml) before being dried for 18 hours at 60° C. to give the unsolvated title compound as a white solid (238 g, 0.89 mol, 72%).

$^1$H-NMR ($D_6$-DMSO, 300 MHz): δ 1.2 (m, 1H), 1.4 (m, 2H), 1.5 (m, 1H), 1.6 (m, 2H), 1.7 (m, 1H), 1.8 (m, 1H), 2.4 (t, 2H), 6.45 (d, 1H), 6.95 (s, 1H), 7.1 (d, 1H), 7.75 (s, 1H).

The invention claimed is:

1. A compound of formula (I):

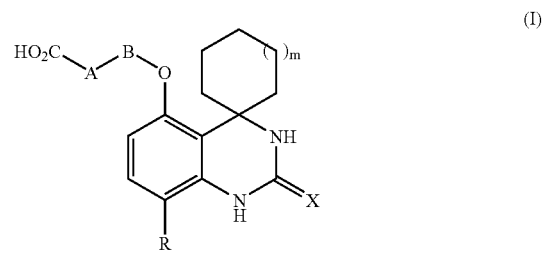

wherein:
   m is 0, 1 or 2;
   X is O, S or N—CN
   R is F, Cl or CN;
   A is a $C_{3-6}$ cycloalkylene group optionally substituted with a $C_{1-4}$ alkyl group; amd
   B is a single bond or a $C_{1-2}$ alkylene group;
or a pharmaceutically acceptable salt, thereof.

2. A compound according to claim 1 wherein m is 1.

3. A compound according to claim 1 wherein X is O.

4. A compound according to claim 1 wherein R is Cl.

5. A compound according to claim 1 wherein A is a cyclobutylene group.

6. A compound according to claim 5 wherein A is a 1,3-cyclobutylene group.

7. A compound according to claim 6 wherein A is a trans-1,3-cyclobutylene group.

8. A compound according to claim 1 wherein B is a single bond.

9. A compound selected from:
   cis-3-[(8'-Chloro-2'-oxo-2',3'-dihydro-1'H-spiro[cyclohexane-1,4'-quinazolin]-5'-yl)oxy]cyclobutanecarboxylic acid;
   trans 3-[(8'-Chloro-2'-oxo-2',3'-dihydro-1'H-spiro[cyclohexane-1,4'-quinazolin]-5'-yl)oxy]cyclobutanecarboxylic acid;
   3-[(8'-fluoro-2'-oxo-2',3'-dihydro-1'H-spiro[cyclohexane-1,4'-quinazolin]-5'-yl)oxymethyl]cyclobutanecarboxylic acid;
   trans-3-[(8'-cyano-2'-oxo-2',3'-dihydro-1'H-spiro[cyclohexane-1,4'-quinazolin]-5'-yl)oxy]cyclobutanecarboxylic acid;
   1-[(8'-fluoro-2'-oxo-2',3'-dihydro-1'H-spiro[cyclohexane-1,4'-quinazolin]-5'-yl)oxymethyl]cyclobutanecarboxylic acid;
   trans-3-[(8'-chloro-2'-oxo-2',3'-dihydro-1'H-spiro[cycloheptyl-1,4'-quinazolin]-5'-yl)oxy]cyclobutanecarboxylic acid; and trans-3-[(8'-chloro-2'-oxo-2',3'-dihydro-1'H-spiro[cyclopentyl-1,4'-quinazolin]-5'-yl)oxy]cyclobutanecarboxylic acid; or a pharmaceutically acceptable salt thereof.

10. A pharmaceutical composition comprising a compound according to claim 1, or a pharmaceutically acceptable salt thereof, and a pharmaceutically acceptable carrier or diluent.

11. A method of treating a condition in a mammal comprising administering to said mammal in need thereof an effective amount of a compound according to claim 1, or a pharmaceutically acceptable salt thereof wherein the condition is neuropathic pain.

12. A method according to claim 11, wherein the disease or condition is pain.

13. A method according to claim 12, wherein the pain is neuropathic pain.

* * * * *